(12) United States Patent
Meyer et al.

(10) Patent No.: US 9,096,882 B2
(45) Date of Patent: Aug. 4, 2015

(54) METHOD OF SELECTING ANTIOXIDANTS FOR USE IN TOPICALLY APPLIED COMPOSITIONS

(71) Applicant: MSD Consumer Care, Inc., Whippany, NJ (US)

(72) Inventors: Thomas A. Meyer, Memphis, TN (US); Donathan G. Beasley, Memphis, TN (US)

(73) Assignee: MSD Consumer Care, Inc., Whippany, NJ (US)

( * ) Notice: Subject to any disclaimer, the term of this patent is extended or adjusted under 35 U.S.C. 154(b) by 0 days.

(21) Appl. No.: 13/651,894

(22) Filed: Oct. 15, 2012

(65) Prior Publication Data

US 2013/0101515 A1    Apr. 25, 2013

Related U.S. Application Data

(63) Continuation of application No. 12/357,006, filed on Jan. 21, 2009, now abandoned.

(60) Provisional application No. 61/023,713, filed on Jan. 25, 2008, provisional application No. 61/114,758, filed on Nov. 14, 2008.

(51) Int. Cl.
*A61K 49/00* (2006.01)
*C12Q 1/02* (2006.01)
*A61K 8/00* (2006.01)
*A61P 17/00* (2006.01)
(Continued)

(52) U.S. Cl.
CPC . *C12Q 1/025* (2013.01); *A61K 8/37* (2013.01); *A61K 8/678* (2013.01); *A61K 8/97* (2013.01); *A61K 49/00* (2013.01); *A61Q 17/04* (2013.01); *G01N 33/5082* (2013.01); *A61K 2800/522* (2013.01)

(58) Field of Classification Search
USPC .......................... 424/9.2, 59, 401, 62; 435/29
See application file for complete search history.

(56) References Cited

U.S. PATENT DOCUMENTS 4,975,272 A    12/1990 Voyt
5,527,519 A *   6/1996 Miksits et al. ............... 423/622
(Continued)

FOREIGN PATENT DOCUMENTS

CN    1086532 A     5/1994
EP    1344516 A1    9/2003
(Continued)

OTHER PUBLICATIONS

Hanson et al., "Obseration and quantification of ultraviolet-induced reactive oxygen species in ex vivo human skin", Photochemistry and Photobiology, 2002, 57-63, vol. 7, No. 1.
(Continued)

*Primary Examiner* — Ernst V Arnold
*Assistant Examiner* — Hong Yu

(57) ABSTRACT

The invention provides antioxidant-containing compositions and methods for confirming antioxidant activity of a composition formulated for topical application to skin. The invention also provides methods for testing a composition for the ability to inhibit both ultraviolet radiation-induced lipid peroxidation on skin and ultraviolet radiation-induced reactive oxygen species formation in the stratum corneum as well as compositions and methods for treating and preventing photodamage to skin.

2 Claims, 6 Drawing Sheets

(51) Int. Cl.
*A61Q 19/02* (2006.01)
*A61K 8/37* (2006.01)
*G01N 33/50* (2006.01)
*A61Q 17/04* (2006.01)
*A61K 8/97* (2006.01)
*A61K 8/67* (2006.01)

(56) References Cited

U.S. PATENT DOCUMENTS

| | | | |
|---|---|---|---|
| 5,817,299 | A | 10/1998 | Manirazman |
| 6,015,548 | A | 1/2000 | Siddiqui et al. |
| 6,231,837 | B1 | 5/2001 | Stroud et al. |
| 6,254,898 | B1 | 7/2001 | Bragaglia |
| 2005/0031655 | A1* | 2/2005 | Karpov ............ 424/401 |
| 2007/0003536 | A1 | 1/2007 | Zimmerman |
| 2007/0020203 | A1 | 1/2007 | Chaudhuri |
| 2007/0140996 | A1 | 6/2007 | Damiani |
| 2007/0160549 | A1 | 7/2007 | Hunt et al. |
| 2007/0231285 | A1 | 10/2007 | Chaudhuri |
| 2008/0213192 | A1 | 9/2008 | Schlesinger et al. |
| 2008/0305059 | A1* | 12/2008 | Chaudhuri ............ 424/62 |

FOREIGN PATENT DOCUMENTS

| | | | |
|---|---|---|---|
| EP | 1591105 | A1 | 11/2005 |
| WO | 99/33439 | A1 | 7/1999 |
| WO | 01/37788 | A1 | 5/2001 |
| WO | 03/007906 | A1 | 1/2003 |
| WO | 2005/016303 | A2 | 2/2005 |
| WO | 2006/124991 | A1 | 11/2006 |

OTHER PUBLICATIONS

WPI World Patent Information Derwent, Derwent, 1994, vol. 30, No. 95, XP002003279, English Translation of CN1086532.

Black et al., Photochem, Photobiol., 1987, 213-221, vol. 46.

Vile et al., Free Radic. Biol. Med., 1995, 721-722, vol. 18.

Chen et al., Proc. Natl. Acad. Sci., 1995, 4337-4341, vol. 92.

International Search Report dated Jun. 15, 2009 for corresponding PCT application (PCT/US2009/031538).

Juglans, Regia, "Gatuline Age Defense" Fragrance Journal, 2001, vol. 1 pp. 97-103.

Patent Abstract of Japanese Patent Application #10-108694 Publication #11-287795 Dated Oct. 19, 1999.

Brown, M. W. et al., Antioxidants—What is their significance in sun protection?, International Journal for Applied Science, Personal Care, Detergents and Specialities, 2003-7, pp. 3-12.

Yasui, H. et al., Real-time chemiluminescent imaging and detection of reactive oxygen species generated in UVB-exposed human skin equivalent model. Biochemical and Biophysical Research Communication 347 (2006) pp. 84-88.

* cited by examiner

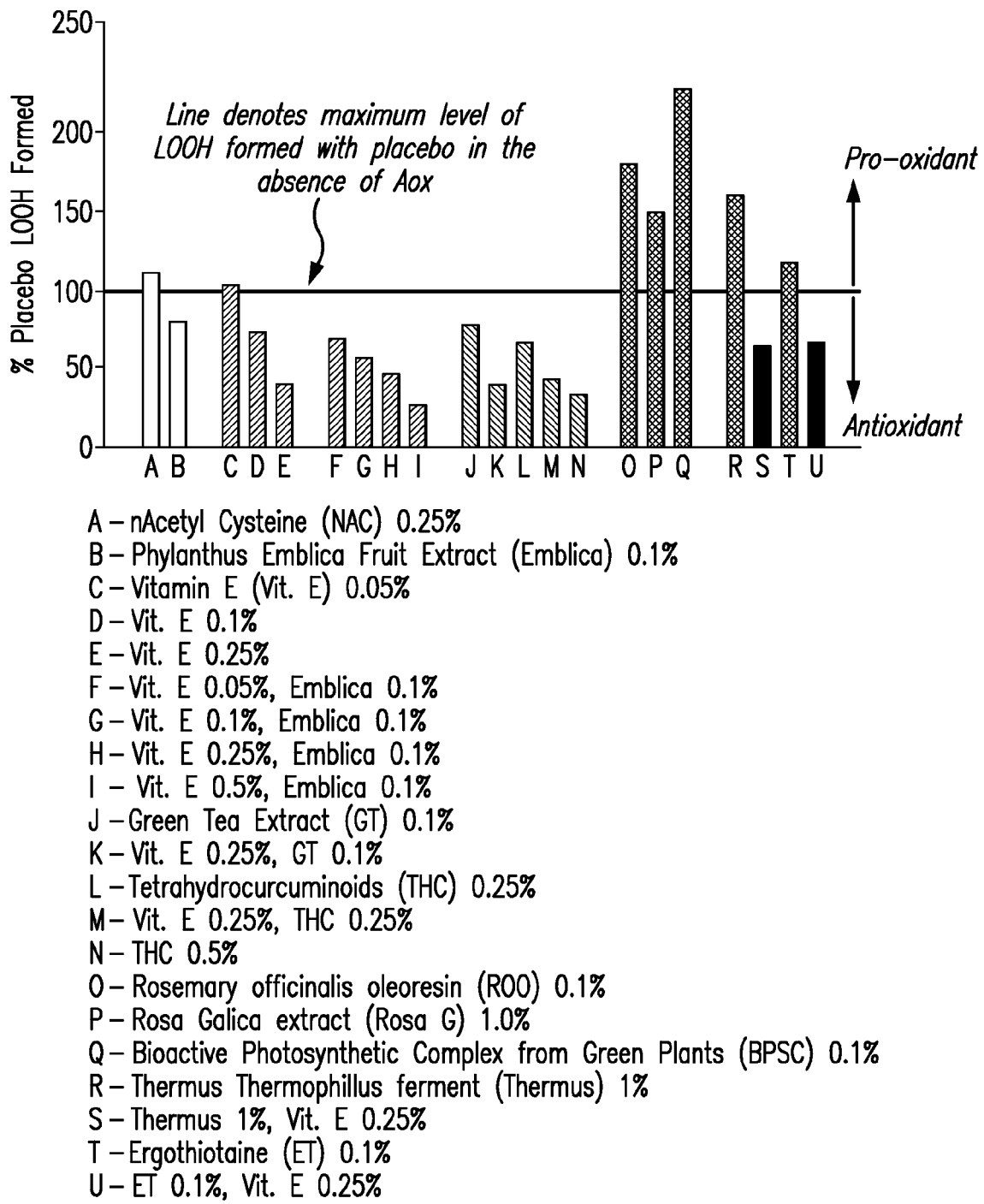

A – nAcetyl Cysteine (NAC) 0.25%
B – Phylanthus Emblica Fruit Extract (Emblica) 0.1%
C – Vitamin E (Vit. E) 0.05%
D – Vit. E 0.1%
E – Vit. E 0.25%
F – Vit. E 0.05%, Emblica 0.1%
G – Vit. E 0.1%, Emblica 0.1%
H – Vit. E 0.25%, Emblica 0.1%
I – Vit. E 0.5%, Emblica 0.1%
J – Green Tea Extract (GT) 0.1%
K – Vit. E 0.25%, GT 0.1%
L – Tetrahydrocurcuminoids (THC) 0.25%
M – Vit. E 0.25%, THC 0.25%
N – THC 0.5%
O – Rosemary officinalis oleoresin (ROO) 0.1%
P – Rosa Galica extract (Rosa G) 1.0%
Q – Bioactive Photosynthetic Complex from Green Plants (BPSC) 0.1%
R – Thermus Thermophillus ferment (Thermus) 1%
S – Thermus 1%, Vit. E 0.25%
T – Ergothiotaine (ET) 0.1%
U – ET 0.1%, Vit. E 0.25%

FIG. 1

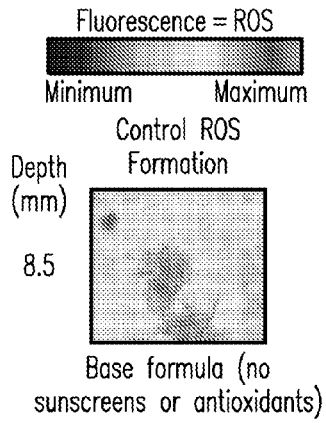

FIG. 2A
Base formula (no sunscreens or antioxidants)
Control ROS Formation
Depth (mm) 8.5

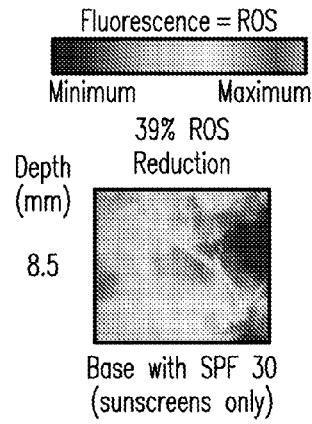

FIG. 2B
Base with SPF 30 (sunscreens only)
39% ROS Reduction
Depth (mm) 8.5

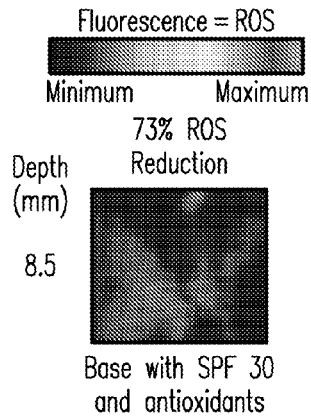

FIG. 2C
Base with SPF 30 and antioxidants
73% ROS Reduction
Depth (mm) 8.5

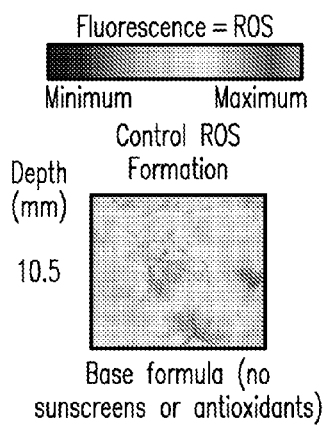

FIG. 2D
Base formula (no sunscreens or antioxidants)
Control ROS Formation
Depth (mm) 10.5

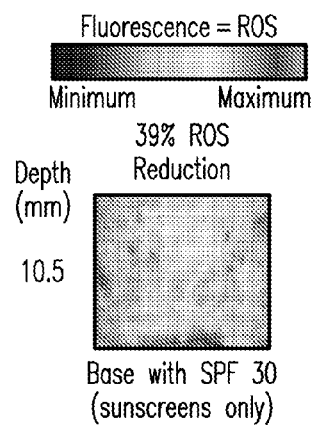

FIG. 2E
Base with SPF 30 (sunscreens only)
39% ROS Reduction
Depth (mm) 10.5

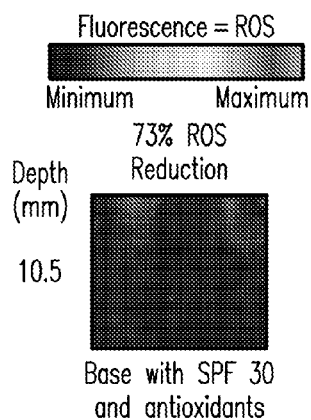

FIG. 2F
Base with SPF 30 and antioxidants
73% ROS Reduction
Depth (mm) 10.5

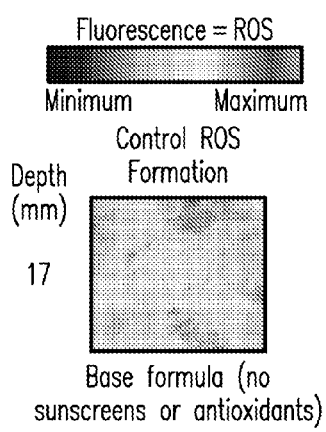

FIG. 2G
Base formula (no sunscreens or antioxidants)
Control ROS Formation
Depth (mm) 17

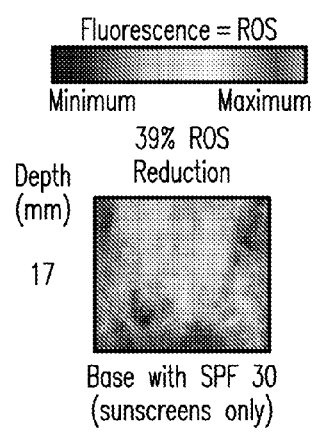

FIG. 2H
Base with SPF 30 (sunscreens only)
39% ROS Reduction
Depth (mm) 17

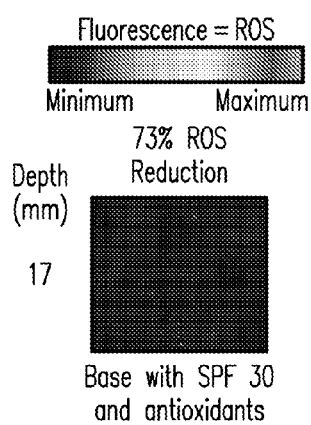

FIG. 2I
Base with SPF 30 and antioxidants
73% ROS Reduction
Depth (mm) 17

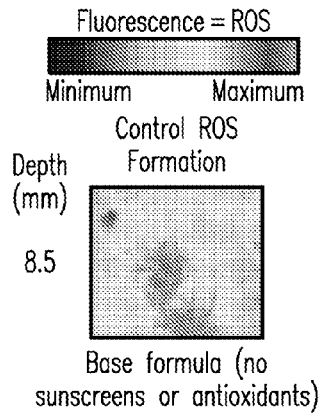

FIG. 3A
Base formula (no sunscreens or antioxidants)
Control ROS Formation
Depth (mm) 8.5

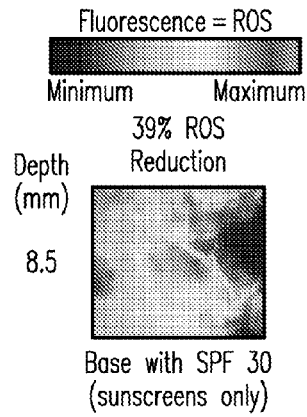

FIG. 3B
Base with SPF 30 (sunscreens only)
39% ROS Reduction
Depth (mm) 8.5

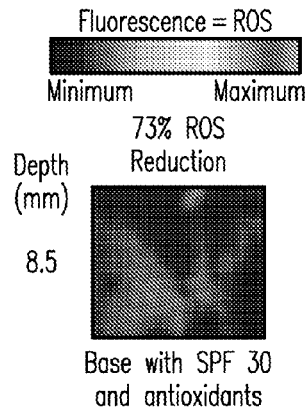

FIG. 3C
Base with SPF 30 and antioxidants
73% ROS Reduction
Depth (mm) 8.5

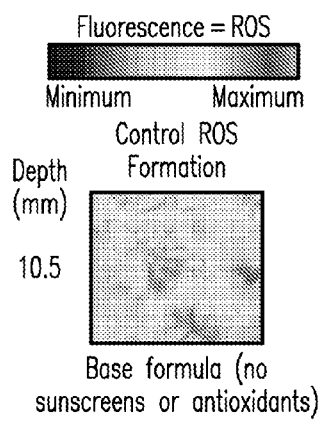

FIG. 3D
Base formula (no sunscreens or antioxidants)
Control ROS Formation
Depth (mm) 10.5

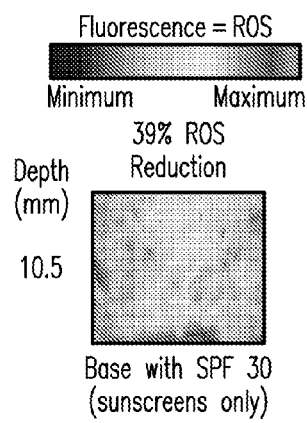

FIG. 3E
Base with SPF 30 (sunscreens only)
39% ROS Reduction
Depth (mm) 10.5

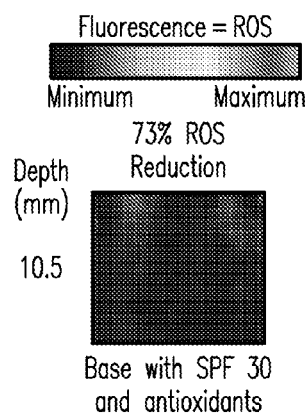

FIG. 3F
Base with SPF 30 and antioxidants
73% ROS Reduction
Depth (mm) 10.5

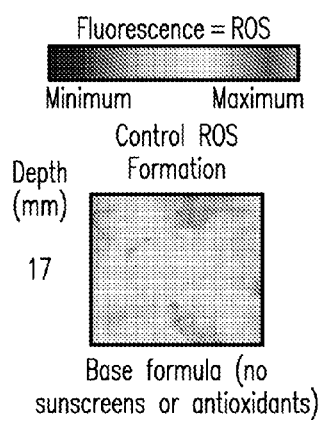

FIG. 3G
Base formula (no sunscreens or antioxidants)
Control ROS Formation
Depth (mm) 17

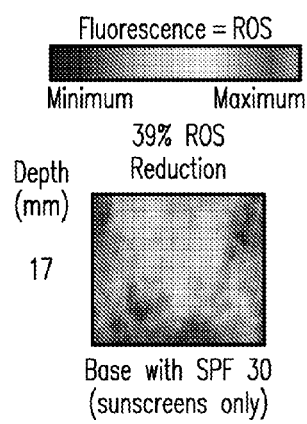

FIG. 3H
Base with SPF 30 (sunscreens only)
39% ROS Reduction
Depth (mm) 17

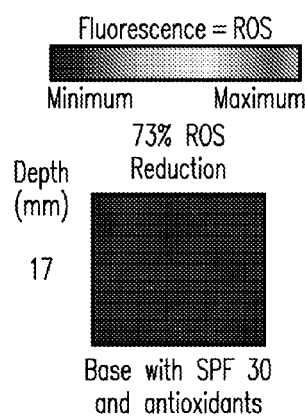

FIG. 3I
Base with SPF 30 and antioxidants
73% ROS Reduction
Depth (mm) 17

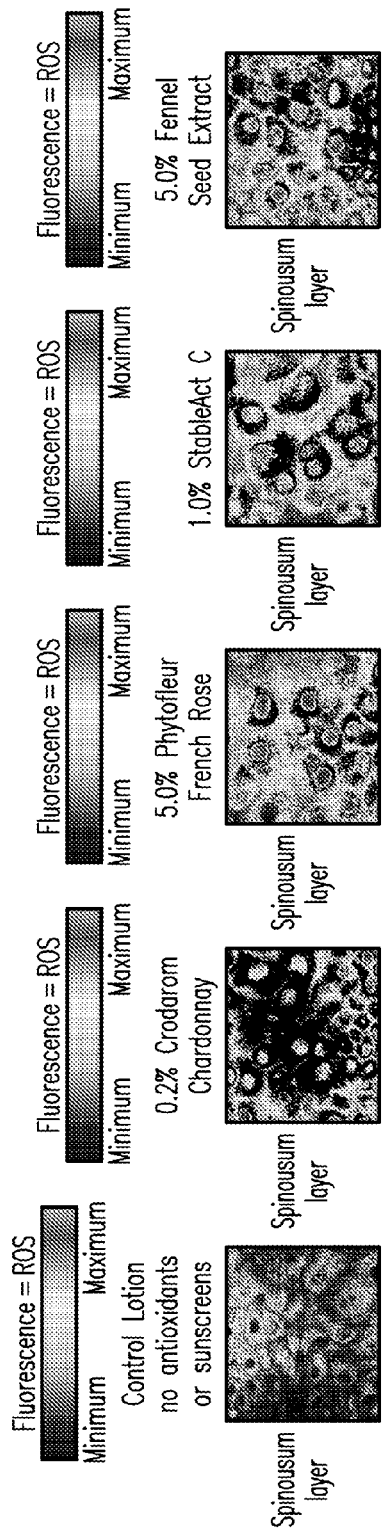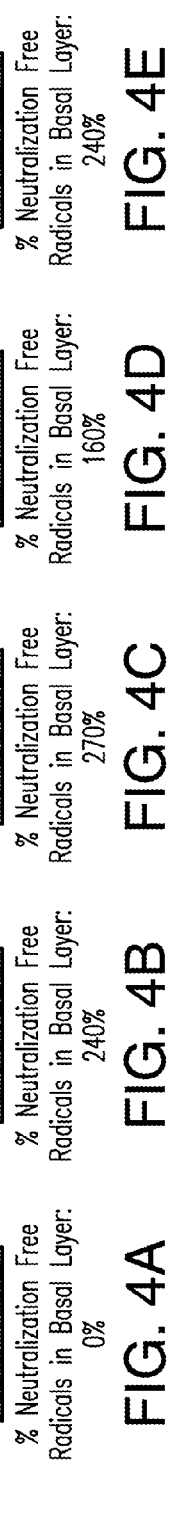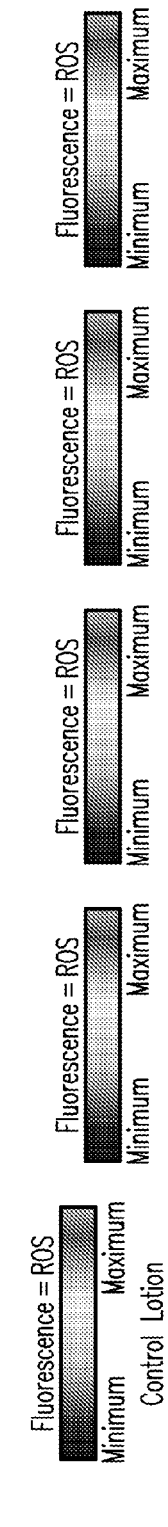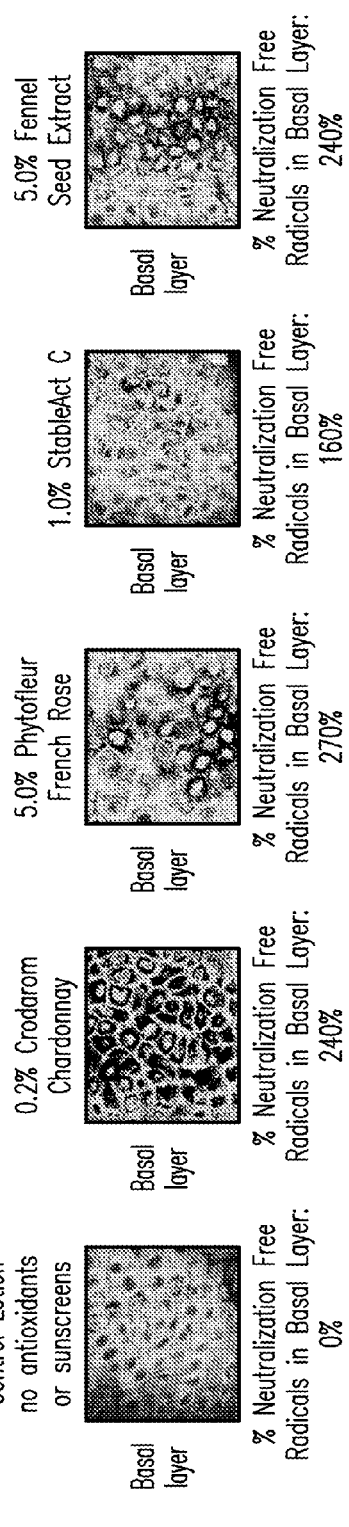

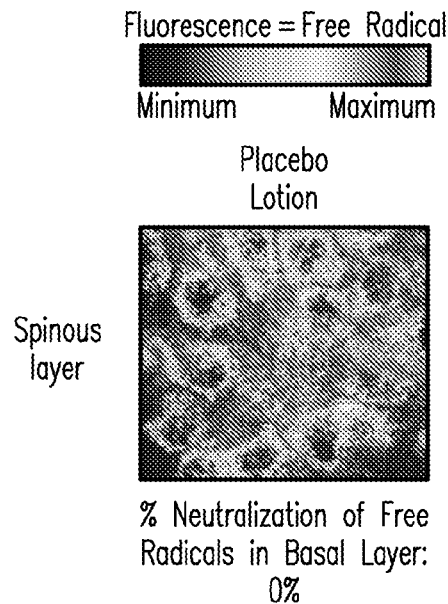

Fluorescence = Free Radical
Minimum   Maximum
Placebo Lotion
Spinous layer
% Neutralization of Free Radicals in Basal Layer: 0%

FIG. 5A

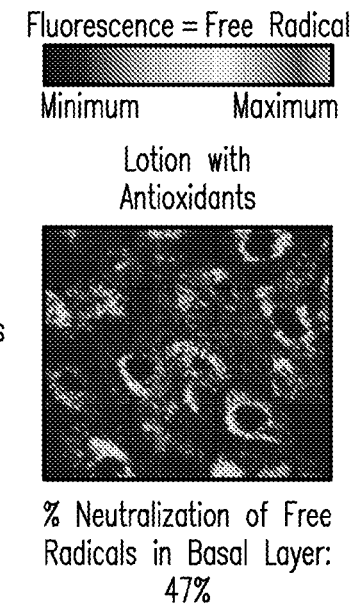

Fluorescence = Free Radical
Minimum   Maximum
Lotion with Antioxidants
Spinous layer
% Neutralization of Free Radicals in Basal Layer: 47%

FIG. 5B

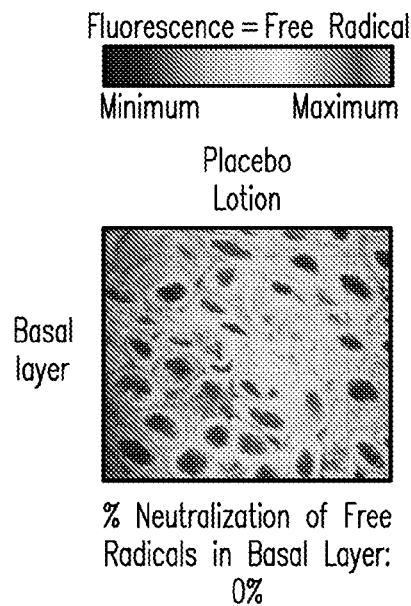

Fluorescence = Free Radical
Minimum   Maximum
Placebo Lotion
Basal layer
% Neutralization of Free Radicals in Basal Layer: 0%

FIG. 5C

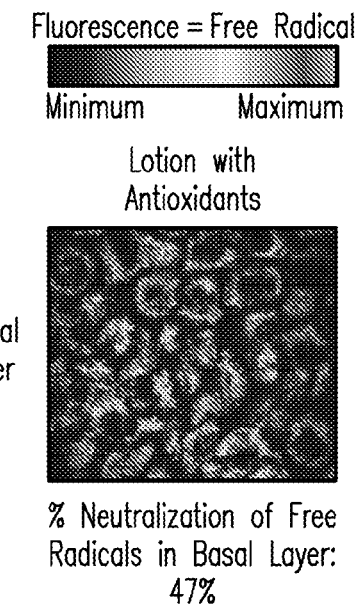

Fluorescence = Free Radical
Minimum   Maximum
Lotion with Antioxidants
Basal layer
% Neutralization of Free Radicals in Basal Layer: 47%

FIG. 5D

METHOD OF SELECTING ANTIOXIDANTS FOR USE IN TOPICALLY APPLIED COMPOSITIONS

This application claims priority to U.S. Provisional Application Nos. 61/023,713, filed Jan. 25, 2008, and 61/114,758, filed Nov. 14, 2008.

FIELD OF THE INVENTION

This invention relates generally to compositions applied topically to skin and hair for protection against ultraviolet radiation. The invention also relates to methods of selecting antioxidants for inclusion in such compositions.

BACKGROUND OF THE INVENTION

Exposure of skin to ultraviolet radiation (UVR) induces formation of free radicals and oxidants (singlet oxygen, hydroxy radical, hydrogen peroxide, peroxynitrite, superoxide anions, etc.) collectively referred to as reactive oxygen species (ROS) (Hanson K M, Clegg R M. *Photochemistry and Photobiology*, 2002, 76(1): 57-63; Black H S. *Photochem. Photobiol.* 1987, 46, 213-221). Formation of UV-induced ROS causes oxidative damage to lipids, proteins and DNA (Vile G F and Tyrrell R M. *Free Radic. Biol. Med*, 1995, 18, 721-722; Chen Q, et al. *Proc. Natl. Acad. Sci. USA*, 1995, 92, 4337-4341).

Under normal circumstances, low levels of ROS are neutralized by skin's constitutive antioxidant defenses. However, research has shown that even sub-erythemal doses of UVR generates such an abundance of ROS that skin's own antioxidant defenses become overwhelmed, resulting in a build up of ROS that are free to cause oxidation, which contributes to acute (immunesuppression and photosensitivity disorders) and chronic (photoaging and skin cancer) forms of skin damage (Thiele J J, et al. *J. Invest. Dermatol*, 1998, 110(5), 756-761; Sander C. S, et al. *J. Invest. Dermatol*, 2002, 118 (4), 618-625; Thiele J. J: *Skin Pharmacol. Appl. Skin Physiol*, 2001, 14 (suppl. 1), 87-91; Sander C S, et al. *International Soc. Dermatol*, 2004, 43, 326-335). EP 1591104 (STADA Pharmaceuticals AG) describes the use of antioxidants in pharmaceutical formulations for protection against infrared radiation.

Antioxidants (Aox) function to neutralize ROS. If the right type and level are present within skin where ROS are being formed, Aox should be able to neutralize ROS before they can attack and oxidize other biomolecules. Accordingly, it would be useful to have a method to determine which topical applied antioxidants can be highly effective at neutralizing UVR-induced reactive oxygen species (ROS) within skin. Further, it would be useful to have a method to distinguish compounds which may only be effective in solution to scavenge free radicals from compounds that may be highly effective antioxidants on skin when exposed to UVR. Further, it would be useful to have a method to determine the correct choice and use-level of antioxidants in sunscreen products to provide extra protection against skin damage caused by UVR-induced ROS. In addition, it would be useful to have a composition that provides protection from UVR-induced ROS both at the skin surface and deep in the epidermis, for example as far as the basal layer. These and other objectives are provided by the invention described herein.

Accordingly the invention described herein provides, inter alia, a method which comprises two unique ex vivo methods to assess the ability of topically applied Aox to provide protection against UVR-induced ROS formation within skin's outer layers. The first method uses microscopy, e.g., fluorescence microscopy, to image and quantify ROS formation in the inner layers of the epidermis, e.g. through to the basal layers, by imaging sections of human skin. The second method quantifies the extent to which the Aox containing composition inhibits peroxidation of lipids in skin's outer layers. This specification also demonstrates that a commonly used laboratory test to measure efficacy of antioxidants in solution to scavenge free radicals is not predictive of an Aox's ability to function effectively on more complex biological substrates like skin exposed to UVR. Thus, the present invention provides an advantage over prior art methods to select Aox for use in sunscreen products to ensure they provide a protective benefit.

All patent and non-patent references cited herein are hereby incorporated in their entirety into this specification by reference thereto. Identification or discussion of any reference in this section or any part of this specification shall not be construed as an admission that such reference is available as prior art to the present application.

SUMMARY OF THE INVENTION

The present invention provides a method for confirming antioxidant activity of a composition formulated for topical application to skin, wherein the method comprises testing the composition for ability to inhibit both ultraviolet radiation-induced lipid peroxidation on skin and ultraviolet radiation-induced reactive oxygen species formation throughout the epidermis.

The invention also provides a method for screening compounds for antioxidant behavior in a composition to be topically applied to skin, wherein the screening method comprises determining the compound's ability to inhibit both ultraviolet radiation-induced skin lipid hydroperoxide formation and ultraviolet radiation-induced reactive oxygen species formation throughout the epidermis.

This invention also provides a composition for application to skin or hair of a subject, wherein the composition comprises an antioxidant compound or combination of antioxidant compounds, wherein the antioxidant compound or combination of antioxidant compounds substantially inhibit both ultraviolet radiation-induced skin lipid peroxidation and ultraviolet radiation-induced reactive oxygen species formation throughout the epidermis.

The invention further provides for a composition for topical application, wherein the composition comprises at least one antioxidant compound that substantially inhibits ultraviolet radiation-induced reactive oxygen species formation in the upper layers of the epidermis and at least one antioxidant compound that substantially inhibits ultraviolet radiation-induced reactive oxygen species formation in the lower layers of the epidermis.

BRIEF DESCRIPTION OF THE DRAWINGS

FIG. 1—shows the extent to which antioxidants (Aox) inhibit UVR-induced formation of lipid hydroperoxides (LOOH) ex vivo using tape strips to collect lipids from human skin in the presence of different types and levels of Aox.

FIGS. 2A through 2I—shows that the addition of antioxidants to sunscreens significantly reduces UV-induced formation of ROS within the stratum corneum. Relative to the control, the SPF 30 sunscreen formula reduced ROS by 39% whereas the SPF 30 formula with 0.5% vitamin E and 0.1% Emblica as antioxidants reduced ROS by 73%. The extent of ROS formation is color coded, with blue indicating low and orange or red indicating high ROS levels.

FIGS. 3A through 3I—shows two photon fluorescence microscopy on skin layers to demonstrate ability of Vitamin E and Emblica antioxidants to reduce UV-induced formation of ROS within the epidermis. A composition containing 0.5% Vitamin E and 0.1% Emblica provide little protection against free radical formation in the lower (basal) layer of the epidermis.

FIGS. 4A through 4J—shows two photon fluorescence microscopy on skin layers to demonstrate effect of various known antioxidants to reduce UV-induced formation of ROS within the epidermis. Tested antioxidant extracts actually increased rather than decreased free radicals when exposed to UVR.

FIGS. 5A through 5D—shows two photon fluorescence microscopy on skin layers to demonstrate effect of various known antioxidants to reduce UV-induced formation of ROS within the epidermis after 1 MED of UVR. A composition containing 0.5% Vitamin E and 0.9% Oxynex ST are shown to inhibit formation of ROS within lower epidermal layers.

DETAILED DESCRIPTION

Figure 6A:
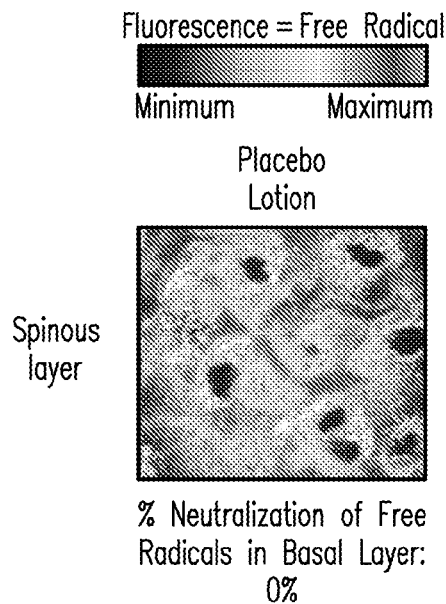
FIGS. 6A through 6D—shows two photon fluorescence microscopy on skin layers to demonstrate effect of various known antioxidants to reduce UV-induced formation of ROS within the epidermis after 4 MED of UVR. A composition containing 0.5% Vitamin E and 0.9% Oxynex ST are shown to inhibit formation of ROS within lower epidermal layers.

The present invention provides a method for confirming antioxidant activity of a composition formulated for topical application to skin, wherein the method comprises testing the composition for ability to inhibit both ultraviolet radiation-induced lipid peroxidation on skin and ultraviolet radiation-induced reactive oxygen species formation throughout the epidermis.

The invention also provides a method for screening compounds for antioxidant behavior in a composition to be topically applied to skin, wherein the screening method comprises determining the compound's ability to inhibit both ultraviolet radiation-induced skin lipid hydroperoxide formation and ultraviolet radiation-induced reactive oxygen species formation throughout the epidermis.

In certain embodiments of the methods of the invention determining inhibition of ultraviolet radiation-induced reactive oxygen species formation in the skin comprises imaging skin throughout the epidermis down to the basal layer using two-photon fluorescence intensity imaging.

In certain embodiments of the method of the invention determining inhibition of UVR-induced skin lipid hydroperoxide formation comprises determining percent lipid hydroperoxide inhibition of the compound in comparison to placebo.

In certain embodiments the methods of the invention comprise the steps of applying to distinct areas of skin of a subject an antioxidant containing composition and a placebo composition to produce an antioxidant skin site containing antioxidant and skin lipids and a placebo skin site containing placebo and skin lipids; applying a strip to the antioxidant skin site and the placebo skin site to produce an antioxidant strip sample containing antioxidant and skin lipids and a placebo strip sample containing placebo and skin lipids; removing said strip samples from the skin and exposing said strip samples to UVR to form a UVR-induced antioxidant/lipid reaction product on the antioxidant strip sample and a UVR-induced placebo/lipid reaction product on the placebo strip sample; separately contacting the antioxidant strip sample and the placebo strip sample with solvent to prepare a first extract containing UVR-induced antioxidant/lipid reaction product and a second extract containing UVR-induced placebo/lipid reaction product; assaying said first and second extracts for lipid hydroperoxide content for each extract; and comparing the lipid hydroperoxide content of the first extract to the lipid hydroperoxide content of the second extract.

In certain embodiments the methods of the invention comprise the further steps of applying placebo to two distinct sites on the skin of the subject; producing strip samples from each site; subjecting strip samples from only one of the two placebo sites to UVR to produce a subset of irradiated placebo strip samples and a subset of nonirradiated placebo strip samples; separately contacting nonirradiated placebo strip samples with solvent to prepare a third extract containing placebo and skin lipids; and assaying said third extract for lipid hydroperoxide content to determine background lipid hydroperoxide formation.

In certain embodiments the methods of the invention comprise comparing the lipid hydroperoxide content of the first extract to the lipid hydroperoxide content of the second extract comprises calculating percent lipid hydroperoxide formation by the following formula:

$$\% \ LF = \frac{(LOOH1 - LOOH3)}{(LOOH2 - LOOH3)} \times 100$$

wherein % LF is the percent lipid hydroperoxide formation, LOOH1 is the lipid hydroperoxide content of the first extract, LOOH2 is the lipid hydroperoxide content of the second extract, and LOOH3 is the lipid hydroperoxide content of the third extract.

The art recognizes numerous compounds as having antioxidant properties. As used herein, the term "antioxidant" refers to compounds or combinations of compounds determined by the methods of the invention to have a % LF that is less than 100%. As used herein the term "prooxidant" refers to compounds or combinations of compounds that have a % LF that is greater than 100%. As demonstrated herein, certain compounds referred to in the art as antioxidants actually have a prooxidant behavior when tested according to the methods of the invention, making them unsuitable as ingredients in compositions for topical application, particularly in sunscreens, unless present in the combinations as described herein.

The compositions of the invention containing the appropriate Aox can comprise any form readily known by those of ordinary skill in the art of preparing cosmetic compositions. Examples of such include, but are not limited to, nonionic vesicle dispersions, emulsions, creams, milks, gels, cream gels, ointments, suspensions, dispersions, powders, solids, sticks, foams or sprays. In certainly preferred embodiments, the composition can comprise an anhydrous or aqueous solid or paste, emulsion, suspension, or dispersion. Preferable forms of the compositions include an oil-in-water emulsion, a water-in-oil emulsion, an alcohol solution, or an aerosol formulation.

Thus, the subject invention also provides a cosmetic composition for topical application to human skin and/or hair, comprising an appropriate Aox and amount of Aox determined by the methods described herein. Non-limiting examples of such cosmetic compositions may include such products as moisturizers, cleansers, conditioners, shampoo, body wash, styling gel/lotion, eye cream and eye liner, blush, mascara, foundation, nail polish, polish remover, eye shadow, lipstick, lip gloss, lip liners, lip balms, makeup remover, nail treatment, foot care compositions, acne treatment, redness/rosacea treatment, varicose/spider vein treatment, anti-aging compositions, sunless tanning compositions, after-sun compositions, concealers, hair color and bleaching compositions, skin fading/lighteners, body firming lotion, shaving cream, after shave, relaxer, antiperspirants and deodorants, exfoliants, scrubs, liquid hand soap, bubble bath, pain and wound treatment compositions, insect repellant, anti-itch and rash cream, styling mousse and foams, perfume, lubricants, body oil, body spray, baby lotion, diaper cream, baby soap, baby shampoo, baby oil, baby wipes, hair-loss treatment, hair spray, depilatory, hair growth inhibitors, hair removal waxes, personal cleansing, cologne, oil controller, and hand sanitizer.

Examples of antioxidants useful in the compositions of the invention include, but are not limited to, Diethylhexyl syringylidene malonate, Vitamin E, diisopropyl vanillidene malonate (also referred to as DIPVM) and related compounds (described in U.S. Pat. Nos. 6,602,515; 6,831,191; 6,936,735; 7,150,876; and 7,166,273), Tetrahydrocurcumenoids, Soybean zymbiozome fermentum, Red clover extract, *Vitis vinifera* (grape) seed extract/Brand B, Green tea extract, *Pikea robusta* extract, Tocopherol (and) *vitis vinifera* (grape) seed extract, *Vitis vinifera* (grape) seed extract/Brand A, *Phylanthus emblica* fruit extract and combinations thereof. Amounts of antioxidants to be added to the compositions of the invention are generally between about 0.01% by weight to about 10.0% by weight, preferably between about 0.1% by weight to about 5.0% by weight. Exact amounts can be determined by one of ordinary skill in the art according to testing methods described herein.

In certain embodiments the composition of the invention can comprise Vitamin E alone as an antioxidant in an amount greater than about 0.05% by weight, in an amount of about 0.1% by weight or greater, in an amount of about 0.25% by weight or greater, and in an amount of about 0.5% by weight or greater. In certain embodiments the composition of the invention can comprise Vitamin E as an antioxidant and at least one additional antioxidant compound.

In certain embodiments the composition of the invention may comprise Vitamin E in combination with a pro-oxidant compound as determined by the methods of the invention, where the presence of Vitamin E in these embodiments will counteract the pro-oxidant effects of these compounds to form an antioxidant combination. In certain embodiments of this composition Vitamin E is present in an amount greater than about 0.05% by weight, in an amount of about 0.1% by weight or greater, in an amount of about 0.25% by weight or greater, and in an amount of about 0.5% by weight or greater. Examples of such pro-oxidant compounds that will be useful in the compositions of the invention that comprise Vitamin E include, but are not limited to, *Rosemary officinalis* oleoresin, *Rosa Gallica* extract, Bioactive Photosynthetic complex from green plants, *Thermus Thermophillus* ferment, ergothiotaine and combinations thereof. Amounts of pro-oxidants to be added to the compositions of the invention are generally between about 0.01% by weight to about 10.0% by weight, preferably between about 0.1% by weight to about 5.0% by weight. Exact amounts can be determined by one of ordinary skill in the art according to testing methods described herein.

In one embodiment the subject invention, the composition can be in the form of an aerosol, wherein the composition is combined with at least one propellant, which may be any suitable gas that can be compressed or liquefied within a spray dispensing canister and which expands or volatilizes to vapor or gas form upon exposure to ambient temperature and pressure conditions to deliver the composition in an aerosol form. Suitable propellants include hydrocarbons having 1 to 5 carbon atoms, including but not limited to methane, ethane, propane, isopropane, butane, isobutane, butene, pentane, isopentane, neopentane, pentene, hydrofluorocarbons (HFCs), chlorofluorocarbons (CFCs), nitrogen, ethers including dimethyl ether, and any mixtures thereof. Those of ordinary skill in the art recognize that in a closed container such as an aluminum can or glass bottle, propellants such as dimethyl ether condense to the liquid state at ambient temperature. Thus, the composition in the aerosol container is liquid formulation which can contain dissolved propellant, undissolved liquid propellant and gaseous propellant. All of this is under pressure due to the vapor pressure of the propellant. In the practice of the subject invention, the propellant can be present in an amount up to about 90 weight percent, preferably from about 2 weight percent to about 50 weight percent, and more preferably about 5 weight percent to about 40 weight percent, most preferably 30 weight percent, based on the total weight of the aerosol composition.

The compositions of the invention can also comprise aerosol foams or so-called mousse compositions. For example, U.S. Pat. No. 6,627,585 describes a mousse-forming cleansing shampoo composition comprising a foamable concentrate comprising at least one surfactant, dispersed particles of a water-insoluble conditioning agent, an aqueous carrier; and an aerosol propellant. U.S. Pat. No. 6,264,964 describes a cosmetic composition including a crosslinked non-emulsifying polysiloxane elastomer and a carboxyvinyl polymer which is in the form of an aerosol foam in a pressurized system. The propellant may be introduced into the mousse composition at the time of filling by using a standard aerosol dispenser, e.g. a spray can arrangement.

The subject invention contemplates the incorporation of Aox with sunscreen actives in sunscreen and sunblock products and any other topically applied composition where the addition of sunscreen active agents and/or Aox would not detract from the efficacy of the product nor affect the sunscreening ability of the sunscreen active agents.

The compositions of the present invention may contain a wide range of additional, optional components which are referred to herein as "cosmetic components", but which can also include components generally known as pharmaceutically active agents. The CTFA Cosmetic Ingredient Handbook, Seventh Edition, 1997 and the Eighth Edition, 2000, which is incorporated by reference herein in its entirety, describes a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, SPF boosters, waterproofing agents, and viscosity increasing agents (aqueous and nonaqueous).

In the practice of the invention, the composition may contain one or more sunscreen active agents. For purposes of the present invention, a "sunscreen active agent" or "sunscreen active" shall include all of those materials, singly or in combination, that are regarded as acceptable for use as active sunscreening ingredients based on their ability to absorb UV radiation. Such compounds are generally described as being UV-A, UV-B, or UV-A/UV-B active agents. Approval by a regulatory agency is generally required for inclusion of active agents in formulations intended for human use. Those active agents which have been or are currently approved for sunscreen use in the United States include organic and inorganic substances including, without limitation, para aminobenzoic acid, avobenzone, cinoxate, dioxybenzone, homosalate, menthyl anthranilate, octyl salicylate, oxybenzone, padimate 0, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum. Examples of additional sunscreen actives that have not yet been approved in the US but are allowed in formulations sold outside of the US include ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. However, as the list of approved sunscreens is currently expanding, those of ordinary skill will recognize that the invention is not limited to sunscreen active agents currently approved for human use but is readily applicable to those that may be allowed in the future.

In one embodiment of the invention the additional sunscreen active agent comprises a photoprotecting effective amount of particulates of at least one inorganic pigment or nanopigment, non-limiting examples of which include titanium dioxide, zinc oxide, iron oxide, zirconium oxide, cerium oxide, or mixture thereof.

The compositions of the invention may also include materials that also increase the SPF of the final composition by such mechanisms as UV radiation scattering and dispersion. Such materials are referred to herein as "UV-radiation scattering agents" and comprise materials that exhibit UV absorbing activity or exhibit no UV absorbing activity. An example of such UV-radiation scattering agents include polymeric materials, such as the product known as SunSpheres™ (Rohm and Haas; Philadelphia, Pa.) which are described by their manufacturer as hollow styrene/acrylates copolymer spheres manufactured by emulsion polymerization. The polymer spheres are said to raise SPF values across the UVA and UVB region by dispersing and/or scattering the incident UV radiation throughout the film of sunscreen present on a surface, such as human skin. It is understood that the spheres cause less UV radiation to penetrate into the skin by redirecting the radiation towards the UV-absorbing sunscreen actives in the sunscreen formulation, where the radiation reacts with the sunscreen active molecules and the energy is dissipated as heat. As used herein, the terms "spheres" or "scattering agents" are not limited by chemical makeup or shape, but comprise any agent that produces the effect of lengthening the path of incident UV radiation, increasing the statistical likelihood that the radiation will contact a sunscreen active molecule, i.e., a UV absorbing active agent. These materials may also include UV absorbing materials that also exhibit scattering properties such as ZnO (examples include Z-Cote™ products available from BASF), $TiO_2$ (examples include the Solaveil™ products available from Uniqema (New Castle, Del., USA)), compounds such as methylene bis-benzotriazolyl tetramethylbutylphenol, ("Tinasorb™ M" available from Ciba Specialty Chemicals, Inc. (Basel, Switzerland). UV radiation scattering agents are typically present in the formulation in amounts up to about 10% by weight, preferably in ranges of about 0.5% to about 7.0% by weight, in particularly preferred ranges of 3% to about 5% by weight.

As used herein, the terms "sunless-tanning agent" or "self-tanning compositions" refer to compositions which, when applied to human skin, impart thereto an appearance similar to that achieved by exposing the skin to natural or artificial sunlight. Examples of sunless tanning active agents are described in U.S. Pat. Nos. 6,482,397, 6,261,541, and 6,231,837. Such sunless tanning compositions typically comprise, in addition to an artificial tanning effective amount of a self tanning agent, effective amounts of a composition coloring agent and a cosmetically acceptable carrier adapted for topical application to human skin. The self tanning agents can also include those compositions generally accepted in the art for application to human skin, and which, when so applied, react therein with amino acids so as to form pigmented products. Such reactions give the skin a brown appearance similar to the color obtained upon exposing it to sunlight for periods of time sufficient to tan the skin. Suitable self tanning agents include, without limitation, alpha-hydroxy aldehydes and ketones, glyceraldehyde and related alcohol aldehydes, various indoles, imidazoles and derivatives thereof, and various approved pigmentation agents. Presently preferred herein as self tanning agents are the alpha-hydroxy aldehydes and ketones. Most preferably, the self tanning agent is dihydroxyacetone ("DHA"). Other suitable self tanning agents include, without limitation, methyl glyoxal, glycerol aldehyde, erythrulose, alloxan, 2,3-dihydroxysuccindialdehyde, 2,3-dimethoxysuccindialdehyde, 2-amino-3-hydroxy-succindialdehyde and 2-benzylamino-3-hydroxysuccindialdehyde.

Suitable emulsifiers or surfactants include pharmaceutically acceptable, non-toxic, non-ionic, anionic and cationic surfactants. Examples of suitable non-ionic surfactants include glycerol fatty acid esters such as glycerol monostearate, glycol fatty acid esters such as propylene glycol monostearate, polyhydric alcohol fatty acid esters such as polyethylene glycol (400) monooleate, polyoxyethylene fatty acid esters such as polyoxyethylene (40) stearate, polyoxyethylene fatty alcohol ethers such as polyoxyethylene (20) stearyl ether, polyoxyethylene sorbitan fatty acid esters such as polyoxyethylene sorbitan monostearate, sorbitan esters such as sorbitan monostearate, alkyl glycosides such as cetearyl glucoside, fatty acid ethanolamides and their derivatives such as the diethanolamide of stearic acid, and the like. Examples of suitable anionic surfactants are soaps including alkali soaps, such as sodium, potassium and ammonium salts of aliphatic carboxylic acids, usually fatty acids, such as sodium stearate. Organic amine soaps include organic amine salts of aliphatic carboxylic acids, usually fatty acids, such as triethanolamine stearate. Metallic soaps include salts of polyvalent metals and aliphatic carboxylic acids, usually fatty acids, such as aluminium stearate. Other classes of suitable anionic surfactants include sulfated fatty acid alcohols such as sodium lauryl sulfate, sulfated oils such as the sulfuric ester of ricinoleic acid disodium salt, and sulfonated compounds such as alkyl sultonates including sodium cetane sulfonate, amide sulfonates such as sodium N-methyl-N-oleyl laurate, sulfonated dibasic acid esters such as sodium dioctyl sulfosuccinate, alkyl aryl sulfonates such as sodium dodecylbenzene sulfonate, alkyl naphthalene sulfonates such a sodium isopropyl naphthalene sulfonate, petroleum sulfonate such as aryl napthalene with alkyl substitutes. Examples of suitable cationic surfactants include amine salts such as octadecyl ammonium chloride, quarternary ammonium compounds such as benzalkonium chloride.

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, *aloe* extracts such as *aloe vera* lipoquinone, synthetic jojoba oils, natural sonora jojoba oils, safflower oil, corn oil, liquid lanolin, cottonseed oil and peanut oil. Preferably, the emollient is a cocoglyceride, which is a mixture of mono, di- and triglycerides of cocoa oil, sold under the trade name of Myritol 331 from Henkel KGaA, or Dicaprylyl Ether available under the trade name Cetiol OE from Henkel KGaA or a $C_{12}$-$C_{15}$ Alkyl Benzoate sold under the trade name Finsolv TN from Finetex. One or more emollients may be present ranging in amounts from about 1 percent to about 10 percent by weight, preferably about 5 percent by weight. Another suitable emollient is DC 200 Fluid 350, a silicone fluid, available Dow Corning Corp.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and *aloe vera* extract.

Other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the formulation.

A humectant is a moistening agent that promotes retention of water due to its hygroscopic properties. Suitable humectants include glycerin, polymeric glycols such as polyethylene glycol and polypropylene glycol, mannitol and sorbitol. Preferably, the humectant is Sorbitol, 70% USP or polyethylene glycol 400, NF. One or more humectants can optionally be included in the formulation in amounts from about 1 percent to about 10 percent by weight, preferably about 5 percent by weight.

A dry-feel modifier is an agent which when added to an emulsion, imparts a "dry feel" to the skin when the emulsion dries. Dry feel modifiers can include talc, kaolin, chalk, zinc oxide, silicone fluids, inorganic salts such as barium sulfate, surface treated silica, precipitated silica, fumed silica such as an Aerosil available from Degussa Inc. of New York, N.Y. U.S.A. Another dry feel modifier is an epichlorohydrin crosslinked glyceryl starch of the type that is disclosed in U.S. Pat. No. 6,488,916.

It may be advantageous to incorporate additional thickening agents, such as, for instance, various Carbopols available from Noveon Co. Particularly preferred are those agents which would not disrupt the lamellar structure in the formulation of the final product, such as non-ionic thickening agents. The selection of additional thickening agents is well within the skill of one in the art.

Additional natural or synthetic substances can also added to the compositions of the invention to protect from or delay its deterioration due to the action of oxygen in the air (oxidation). They may also reduce oxidation reactions in skin tissue. Such substances prevent oxidative deterioration which may lead to the generation of rancidity and nonenyzymatic browning reaction products. Typical suitable substances include propyl, octyl and dodecyl esters of gallic acid, butylated hydroxyanisole (BHA, usually purchased as a mixture of ortho and meta isomers), butylated hydroxytoluene (BHT), green tea extract, uric acid, cysteine, pyruvate, nordihydroguaiaretic acid, Vitamin A, Vitamin E and Vitamin C and their derivatives. One or more such substances can optionally be included in the composition in an amount ranging from about 0.001 to about 5 weight percent, preferably about 0.01 to about 0.5 percent.

Chelating agents are substances used to chelate or bind metallic ions, such as with a heterocylic ring structure so that the ion is held by chemical bonds from each of the participating rings. Suitable chelating agents include ethylene diaminetetraacetic acid (EDTA), EDTA disodium, calcium disodium edetate, EDTA trisodium, albumin, transferrin, desferoxamine, desferal, desferoxamine mesylate, EDTA tetrasodium and EDTA dipotassium, or combinations of any of these.

Fragrances are aromatic substances which can impart an aesthetically pleasing aroma to the sunscreen composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. One or more fragrances can optionally be included in the sunscreen composition in an amount ranging from about 0.001 to about 5 weight percent, preferably about 0.01 to about 0.5 percent by weight. Additional preservatives may also be used if desired and include well known preservative compositions such as benzyl alcohol, phenyl ethyl alcohol and benzoic acid, diazolydinyl, urea, chlorphenesin, iodopropynyl and butyl carbamate, among others.

The compositions of the invention can further comprise skin protectant active agents. Suitable examples include (with preferred weight percent ranges), Allantoin (0.5 to 2 percent); Aluminum hydroxide gel (0.15 to 5 percent); Calamine (1 to 25 percent); Cocoa butter (greater than 50); Cod liver oil (5 to 14 percent); Colloidal oatmeal; Dimethicone (1 to 30 percent); Glycerin (20 to 45 percent); Hard fat (greater than 50); Kaolin (4 to 20 percent); Lanolin (12.5 to 50 percent); Mineral oil (greater than 50 percent); Petrolatum (greater than 30 percent); Sodium bicarbonate; Topical starch (10 to 98 percent); White petrolatum (greater than 30 percent); Zinc acetate (0.1 to 2 percent); Zinc carbonate (0.2 to 2 percent); and Zinc oxide (1 to 25 percent).

The compositions of the invention may further include insect repelling components. The most widely used insect repelling active agent for personal care products is N,N-Diethyl-m-toluamide, frequently called "DEET" and available in the form of a concentrate containing at least about 95 percent DEET. Other synthetic chemical repellents include ethyl butylacetylaminoproprionate (also known as IR 3535), dimethyl phthalate, ethyl hexanediol, indalone, di-n-propyl-isocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

Topical application of the compositions of the invention described herein to the hair or skin of a human will provide enhanced protection against deleterious effects of ultraviolet radiation (UVR). Thus, the subject invention further provides a method for protecting human skin and/or hair against the deleterious effects of solar radiation, more particularly UVR, which method comprises topically applying thereto an effective amount of the compositions as described herein containing sunscreens and one or more antioxidants. An esthetically beneficial result of exposure of skin to UVR (i.e., light radiation wavelengths of from 280 nm to 400 nm) is the promotion of tanning of the human epidermis. Another benefit of sun exposure comes from production of vitamin D within the skin. UVR is typically divided into UV-A (light wavelengths from 320 to 400 nm) and UV-B (wavelengths ranging from 280 to 320 nm) regions. Overexposure to UV-B irradiation is generally understood to lead to skin burns and erythema. In addition, overexposure to UV-A radiation may cause a loss of elasticity of the skin and the appearance of wrinkles, promoting premature skin aging. Such irradiation promotes triggering of the erythemal reaction or amplifies this reaction in certain individuals and may even be the source of phototoxic or photoallergic reactions. It is increasingly believed that overexposure to UV-A may also lead to melanoma. Thus, the application of the compositions of the invention to the skin and/or hair of an individual will provide enhanced UVR photoprotection (UV-A and/or UV-B) of the skin and/or hair of the individual.

The invention further provides a method of treating and/or reversing photodamage of skin by applying the compositions of the invention to skin that will be or has been exposed to UVR. The term "treating and/or reversing photodamage" is intended to mean obtaining an improvement in one or more attributes of skin condition such as dryness, texture, elasticity/firmness/resiliency, lines/wrinkles, skin tone/clarity, uniformity of pigmentation, and/or erythema which condition is exacerbated by exposure to UVR.

The sunscreen containing compositions of the invention are intended to provide a sun protection factor (SPF) rating of at least 2, with additional preferable embodiments having a sun protection factor of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. The sunscreen containing compositions of the invention are also intended to provide U.S. FDA UV-B "star ratings" of at least one star, at least two stars, at least three stars and up to four stars.

The invention will be further described by means of the following examples, which are not intended to limit the invention, as defined by the appended claims, in any manner.

EXPERIMENTAL

DPPH (α,α-diphenyl-β-picrylhydrazyl) Free Radical Test

DPPH is a stable free radical that when dissolved in solution forms an intense purple color. When reduced by an antioxidant, the purple color fades until it finally disappears as DPPH is completely reduced. The extent to which the color fades can be easily measured and used to rank the relative effectiveness of different materials purported to have antioxidant properties.

Measurements were recorded for antioxidant raw materials in simple methanol solutions. Samples were prepared by dissolving antioxidants at various concentrations in methanol. After sample preparation, 125 µl of the sample or pure methanol as a control were pipetted into sample test tubes followed by 2 ml of methanol and vortexed. Then 2 ml of DPPH stock solution (0.25 mM in methanol) was added to each tube (giving a total volume of 4.125 ml for each sample) and vortexed. Immediately after addition of DPPH, test tubes were covered and placed into a 30° C. water bath for 20 minutes. After the 20 minute incubation, the absorbance of each sample was recorded at 517 nm using a Perkin Elmer Lambda 40 spectrophotometer. All samples were prepared in triplicate and their mean absorbance values were used to express the efficacy of antioxidants at various concentrations in terms of antioxidant reducing units (ARU) by using the following equation:

$$ARU = (\text{Absorbance Methanol Control} - \text{Absorbance sample}) \times 10$$

ARU values range in magnitude from 0 for "no" efficacy to about 15 for raw materials that have high antioxidant efficacy.

Antioxidant effectiveness for a variety of oil and water-soluble raw materials purported to have antioxidant properties appears in Table 1. The raw materials include well-known antioxidants such as vitamin E, in addition to popular plant extracts such as green tea, rose, grape and mushrooms, among others. Effectiveness is expressed as antioxidant reducing units (ARU), which span values of 0 for no efficacy to 12 for antioxidants with high efficacy to reduce the DPPH radical. Examples of both oil and water soluble antioxidants spanned this range.

TABLE 1

| Antioxidant | Level (%) | ARU | Solubility |
| --- | --- | --- | --- |
| Rosemary *officinalis* oleoresin [ROO]* | 0.1 | 0.0 | O |
| Arjunolic acid (1%) | 1.0 | 0.4 | O |
| Diethylhexyl syringylidene malonate | 1.0 | 5.7 | O |
| Vitamin E [Vit. E]* | 0.5 | 6.5 | O |
| Tetrahydrocurcumenoids [THC]* | 0.5 | 9.0 | O |
| Bioactive photosynthetic complex from green plants [BPSC]* | 0.1 | 0.0 | W |
| *Thermus thermophillus* ferment [*Thermus*]* | 1.0 | 0.0 | W |
| Ergothiotaine [ET]* | 0.1 | 0.0 | W |
| *Rosa gallica* extract [*Rosa* G]* | 1.0 | 0.0 | W |
| *Foeniculum vulgare* (fennel) seed Extract | 5.0 | 0.0 | W |
| Soybean zymbiozome fermentum | 1.0 | 0.0 | W |
| Shitake mushroom extract | 5.0 | 0.0 | W |
| *Helianthus annuus* (sunflower) extract | 1.0 | 0.0 | W |
| Red clover extract | 1.0 | 0.6 | W |
| *Vitis vinifera* (grape) seed extract/Brand B | 0.1 | 1.9 | W |
| Green tea extract [GT]* | 0.1 | 2.2 | W |
| *Pikea robusta* extract | 1.0 | 2.2 | W |
| Tocopherol (and) *vitis vinifera* (grape) seed extract | 1.0 | 7.6 | W |
| n-Acetyl cysteine [NAC]* | 0.1 | 9.9 | W |
| *Vitis vinifera* (grape) seed extract/Brand A | 0.1 | 11.5 | W |
| *Phylanthus emblica* fruit extract [*Emblica*]* | 0.1 | 11.5 | W |

Compared with vitamin E, some materials clearly possess lower (ARU<6.5) while others higher (ARU>6.5) antioxidant effectiveness. Based upon ARU values alone, it would be expected that antioxidants with ARU>6.5 would be superior to vitamin E in their ability to neutralize UVR-induced formation of ROS within the skin. However, recognizing that ROS covers a wide range of reactive compounds, including free radicals but also other oxidants like hydrogen peroxide, singlet oxygen or peroxynitrite, results from the DPPH free radical test may not adequately predict antioxidant effectiveness on skin that is exposed to UVR. We, therefore, selected several antioxidants (denoted with *) from Table 1 covering a range of ARU values to test in model systems that more closely mimic intact human skin exposed to UVR to understand if Aox effectiveness in solution as measured by the DPPH free radical test translated to similar levels of effectiveness on skin.

Ex Vivo Tape Strip Method to Assess Antioxidants Ability to Inhibit Lipid Peroxidation.

To determine if antioxidants (Aox) maintain their effectiveness on skin in the presence of UVR, we devised a novel and more relevant model that utilizes human skin lipids as substrates for UVR-induced peroxidation. Lipids removed from skin on broad pieces of tape serve as the substrates for subsequent exposure to UVR. By applying a standard lotion with or without Aox to skin prior to tape-stripping, skin lipids can be collected on tape strips in the presence or absence of Aox that essentially maintains the same proximity that lipids and Aox had on skin. Following UVR exposure, the extent to which the presence of Aox protect lipids against peroxidation from ROS can be measured relative to lipids in the absence of antioxidants.

Human volunteers were recruited for the test and asked not to apply any products to their arms for at least two days before the test Prior to any product treatments, inner aspects of subjects' left and right forearms were wiped with a Kimwipe™ moistened with isopropanol to remove any residues that might be on the surface of the skin. Arms were wiped only once applying gentle pressure and then allowed to dry at least 10 minutes before proceeding. A template (90 mm×50 mm) was positioned on each inner forearm such that two areas could be clearly delineated. Using a superfine tip Sharpie™ pen, a mark was placed at each corner of the template to outline each application site, with two sites delineated per forearm. Using a fingercot, either placebo or antioxidant lotion was applied (100 mg) to a delineated site on a forearm. Care was taken to insure that products were applied evenly within the entire application area. After application, sites were allowed to air-dry for 30 minutes during which subjects were instructed not to allow any clothing to come into contact with test areas.

After lotions dried for 30 minutes, each site was tape-stripped using a 4.0 inch piece of Scotch® Brand No. 800 Prescription Label tape (1.5 inches wide). One end of the tape was folded over to provide an edge that did not adhere to skin for easy removal. The piece of tape was positioned over a site and then using a finger the tape was gently pressed onto the skin to make good contact. Then the tape was quickly removed from the subject's arm. After removal, all tapes were stored in a dark location such as a drawer until they were either irradiated with UV or extracted with isopropanol (i.e., nonirradiated control). Select tape strips of skin of each subject were irradiated with a dose of 10 joules/cm$^2$ using a 1000 W Xe arc solar simulator (WG320 filtered). An Optronics OL-754 spectroradiometer was used to adjust the output of the solar simulator to deliver a constant dose of UVR. After irradiation, tapes were trimmed to a length of three inches and placed in 20 ml glass scintillation vials. Then four ml of isopropanol was added to each vial, after which they were capped. Vials were then shaken vigorously again and placed in a $-20°$ C. freezer to extract overnight. The next day samples were shaken before aliquots were removed for lipid hydroperoxide (LOOH) analysis.

Each tape extract was assayed for total LOOH content using a Lipid Hydroperoxide Assay Kit (Kamiya Biomedical Company, Thousand Oaks, Calif.) following manufacturer's directions. Lipid hydroperoxides were then quantitated by measuring methylene blue formation at 675 nm using a spectrophotometer. Standard curves were prepared using cumene hydroperoxide and were linear over the range of LOOH detected in these experiments. Each extract was assayed in triplicate and the results presented here represent the mean of those analyses. The standard deviations were typically less than 10%.

The extent to which antioxidant (Aox) or placebo lotions inhibited UVR-induced lipid hydroperoxide (LOOH) formation was calculated by inserting the values of LOOH determined from the four application sites on each volunteer into the following equation:

$$\% \ LOOH \ \text{Formation} = \frac{(LOOH \ \text{Aox irradiated} - LOOH \ \text{unirradiated placebo})}{(LOOH \ \text{irradiated placebo} - LOOH \ \text{unirradiated placebo})} \times 100$$

Calculation of "% LOOH formation" enables each subject to be his own internal control and normalizes the data with respect to the area of the tape (3 inches) used to strip skin. In this way, values for % LOOH formation can be compared between sites on different people.

Data were analyzed using paired t-tests to determine if antioxidant or placebo treatments yielded significantly different results. An alpha level of 0.05 and a power of 80% was used for all statistical tests.

Results for select antioxidants (* in Table 1) to protect lipids from UVR-induced ROS formation appear in FIG. 1, which reveals several striking features. Both water and oil soluble materials can protect lipids against UVR-induced peroxidation; however, the raw material must be able to partition into the lipid bilayers to be protective. Vitamin E protects skin lipids in a dose dependant manner (yellow bars). Tetrahydrocurcurminoids (THC) are as efficacious as Vitamin E. Vitamin E in combination with Emblica, GT or THC (orange bars) protect about as well as Vit. E alone (yellow bars). Surprisingly, some materials (red bars) increase rather than decrease lipid hydroperoxide (LOOH) levels, acting as pro-oxidants as opposed to antioxidants. Addition of Vitamin E can reduce pro-oxidant properties (blue bars) of antioxidants but not to the same degree as observed with Vitamin E alone.

These results demonstrate that the DPPH free radical test by itself is not predictive of an Aox's ability to function effectively on skin to protect lipids from peroxidation from UV-induced ROS formation.

Two-Photon Fluorescence Microscopy Imaging of Stratum Corneum.

Two-photon fluorescence intensity imaging was performed ex vivo on pieces of human breast skin (~0.5 cm×0.5 cm) to detect and quantify levels of UV-induced reactive oxygen species (ROS) in the stratum corneum using procedures described previously (Hanson K M, Clegg R M. *Photochemistry and Photobiology*, 2002, 76(1): 57-63). Test formulas were applied to the surface of skin samples at 2 mg/cm$^2$ using the tip of a glass rod. Prior to irradiation, skin samples were incubated in 100 μmolar dihydrorhodamine (DHR) in phosphate-buffered saline-ethanol. DHR partitions into the tissue where it reacts with UV-induced ROS to produce highly fluorescent rhodamine-123, which is subsequently imaged and quantified as a measure of UV-induced ROS formation. At least two unique areas are imaged from each skin sample and at each depth. A base formula without sunscreen actives or antioxidants was used as a control The images shown in FIG. 2 demonstrate the extent of UV-induced ROS formation that resulted within the full thickness of stratum corneum after each formula was applied to intact pieces of human skin and irradiated. The images demonstrate clearly that exposure to 4 MEDs of full spectrum UV radiation generates abundant ROS formation. Application of an SPF 30 broad spectrum sunscreen formula prior to irradiation reduced ROS formation by 39% relative to the control formula by virtue of its ability to absorb UV before it can interact with skin to generate ROS. However, application of an SPF 30 formula plus antioxidants (0.5% vitamin E, 0.1% Emblica) reduced ROS formation by a total of 73% relative to the control formula, which represents an additional reduction in ROS of 34% compared with the formula that only contains the sunscreen actives.

Thus, these results demonstrate convincingly that addition of antioxidants of the right type and level can complement sunscreens as an additional strategy to protect skin from the harmful effects of UV-induced ROS formation. Exposure of skin to UVR can generate an abundance of ROS even through a protective layer of broad spectrum SPF 30 sunscreen. With the power to neutralize ROS, antioxidants (Aox) can provide measurable and meaningful levels of protection against the damaging effects of ROS and in this way significantly augment the protective power of sunscreens provided, however, that Aox for use in sunscreens are selected appropriately. Protection Through Basal Layer with Antioxidant Combination A. Lipid Peroxidation Inhibition Vitamin E is highly effective at neutralizing UV-induced ROS in the outer layer of epidermis, the stratum corneum. Placebo and experimental formulations were prepared to compare the formulations' ability to inhibit lipid peroxidation. The formulations used are shown in Table 2.

TABLE 2

Placebo and Antioxidant Lotions Used in Tape Strip Studies

| Ingredient | Placebo Lotion %, w/w | Placebo Lotion %, w/w | Antioxidant Lotion %, w/w | Antioxidant Lotion %, w/w |
|---|---|---|---|---|
| Part A | | | | |
| USP purified water | 86.75 | 86.75 | 86.15 | 85.35 |
| Simulgel NS | 2.00 | — | — | 2.00 |
| Sepigel 305 | — | 2.00 | 2.00 | — |
| Sodium cetearyl sulfate | 0.250 | 0.25 | 0.25 | 0.25 |
| Emblica | | | 0.1 | — |
| Part B | | | | |
| Octyl palmitate | 10.0 | — | — | 10.0 |
| Isopropyl laurate | — | 10.0 | 10.0 | — |
| Vitamin E | — | — | 0.50 | 0.50 |
| Oxynex ST | — | — | — | 0.90 |
| Part C | | | | |
| Germaben II | 1.00 | 1.00 | 1.00 | 1.00 |

The formulations were prepared by adding sodium cetearyl sulfate to the water of part A and mixing, followed by addition of either Simulgel NS or Sepigel 305 and mixing thoroughly. Then the Part B ingredients were added with mixing, followed by Germaben II in Part C. After all ingredients are added, the emulsion was mixed thoroughly.

Using the ex vivo tape strip method as described above, a composition containing vitamin E, by itself or in combination with Emblica, was found to be highly effective at protecting skin's lipids on its outer surface from UV-induced oxidation mediated by ROS (Table 3).

TABLE 3

| Antioxidant | % Inhibition of LOOH |
|---|---|
| 0.05% vit E | −3.40 |
| 0.10% vit E | 28.4 |
| 0.25% vit E | 61.0 |
| 0.1% Emblica | 19.6 |
| 0.3% Emblica | 10.9 |
| 0.05% vit E + 0.1% Emblica | 28.1 |
| 0.10% vit E + 0.1% Emblica | 47.8 |
| 0.25% vit E + 0.1% Emblica | 65.0 |
| 0.50% vit E + 0.1% Emblica | 74.4 |

B. Two Photon Fluorescence Microscopy

Two photon fluorescence microscopy was then conducted on a formulation containing Vitamin E and Emblica to determine ability to inhibit formation of ROS. The methods used were similar to those as described above, using confocal microscopy to visualize cells at different depths within intact pieces of skin and then fluorescence to quantify the extent of ROS formation. In the present experiment, however, instead of using human breast skin, the skin used was the EpiDerm™ Skin Model (MatTek Corporation, Mass. USA), which consists of normal, human-derived epidermal keratinocytes which have been cultured to form a multilayered, highly differentiated model of the human epidermis. Ultrastructurally, the EpiDerm™ Skin Model closely parallels human skin, thus providing a useful in vitro model to study the ability of antioxidants to neutralize ROS formed during exposure to UVR down to the basal layer.

Prior to UVR exposure, pieces of EpiDerm™ skin were treated with dihydrorhodamine, which partitions throughout the aqueous and lipid regions of the tissue. Upon exposure to UVR, dihydrorhodamine in the tissue reacts chemically with ROS wherever it forms to generate a highly fluorescent molecule. The fluorescence is subsequently detected and quantified to provide an indication of the level of UV-induced ROS formed in deeper layers of the skin. By applying antioxidants topically before irradiation ROS formation can be measured and compared to the ROS formed after a placebo lotion without antioxidants was applied to the skin. In this way, the efficacy of antioxidants to neutralize ROS within deeper layers of the skin can be measured and their relative efficiencies established.

Using this method, the experimental formulation containing vitamin E and emblica was tested to determine its ability to neutralize ROS within the basal layer or bottom layer of the epidermis after exposure to 4 MED. The experimental formulation and placebo lotion used in this experiment were prepared as follows.

TABLE 4

| | Placebo Lotion | |
|---|---|---|
| Part A | USP purified water | 60.04% |
| | Acrylates/c10-30 alkyl acrylate crosspolymer | 0.30% |
| Part B | Propylene glycol | 5.00% |
| | Disodium EDTA | 0.01% |
| | Triethanolamine, 99% | 0.35% |
| Part C | Octyl palmitate | 29.00% |
| | PVP/Eicosene copolymer | 2.00% |
| | Stearic acid | 0.50% |
| | Polyglyceryl-3 distearate | 0.29% |
| | Methylparaben | 0.30% |
| | Sorbitan isostearate | 0.71% |
| | Propylparaben | 0.10% |
| | Dimethicone, 50 cst | 0.40% |
| Part D | Benzyl alcohol | 1.00% |

TABLE 5

| | Antioxidant Lotion | |
|---|---|---|
| Part A | Usp purified water | 58.54% |
| | Acrylates/c10-30 alkyl acrylate crosspolymer | 0.30% |
| Part B | Propylene glycol | 5.00% |
| | Disodium EDTA | 0.01% |
| | Triethanolamine, 99% | 0.35% |
| Part C | Octyl palmitate | 29.00% |
| | Pvp/eicosene copolymer | 2.00% |
| | Stearic acid | 0.50% |
| | Polyglyceryl-3 distearate | 0.29% |
| | Methylparaben | 0.30% |
| | Sorbitan isostearate | 0.71% |
| | Vitamin E, dl alpha tocopherol | 0.50% |
| | *Emblica* | 0.10% |
| | Propylparaben | 0.10% |
| | Dimethicone, 50 cst | 0.40% |
| Part D | Benzyl alcohol | 1.00% |

A water phase was created by adding Acrylates/C10-30 Alkyl Acrylate Crosspolymer to water of Part A while stirring and mixed until clear and lump-free. While mixing, the propylene glycol and disodium EDTA were added to the water phase mixture of Part A and mixed well for 10 minutes. Triethanolamine of Part B was then added to the water phase mixture and continued mixing well. Separately an oil phase was created by mixing the ingredients of Part C together and heat to 140-145° F. while mixing well. The oil phase was then added to the water phase and continued mixing to form an emulsion. The emulsion was cooled to room temperature and then benzyl alcohol of part D was added to the cool emulsion and mixed thoroughly. Additional water was added QS to weight. The difference between the placebo and experimental formulation was the addition of antioxidants into the oil phase.

As shown in FIG. 3, while highly effective in the outer layers of the epidermis, the combination of 0.5% vitamin E and 0.1% emblica only reduced ROS formation in the basal layer of epidermis by about 5%.

We next evaluated a wide range of ingredients used within the cosmetic industry for their claimed antioxidant ability, and were surprised to observe that many of them behaved as pro-oxidants at the basal layer on skin exposed to UVR. As demonstrated in FIG. 4, rather than decreasing levels of ROS, these ingredients increased levels of ROS by up to 250% within the basal layer of epidermis relative to a placebo lotion without any antioxidant. Many of these ingredients that behaved as pro-oxidants represented natural plant extracts from fennel seeds, rose and white grapes. Together these results demonstrated that antioxidants used in suncare products where intentional sun exposure occurs need to be selected judiciously. Moreover the tests demonstrate that the methods of the invention reveal that not all ingredients identified as "antioxidants" provide actual antioxidant properties in real world use with UVR exposures.

We next tested an experimental formulation containing a combination of antioxidant vitamin E and diethylhexyl syringylidene malonate (Oxynex® ST, Merck KGaA, Germany) to determine whether the combination would be effective protection against UV-induced ROS formation throughout the epidermis. Placebo and experimental formulations were prepared similar to the methods described above:

TABLE 6

| | Placebo Lotion | |
|---|---|---|
| Part A | USP purified water | 60.04% |
| | Acrylates/c10-30 alkyl acrylate crosspolymer | 0.30% |
| Part B | Propylene glycol | 5.00% |
| | Disodium EDTA | 0.01% |
| | Triethanolamine, 99% | 0.35% |
| Part C | Octyl palmitate | 29.00% |
| | PVP/Eicosene copolymer | 2.00% |
| | Stearic acid | 0.50% |
| | Polyglyceryl-3 distearate | 0.29% |
| | Methylparaben | 0.30% |
| | Sorbitan isostearate | 0.71% |
| | Propylparaben | 0.10% |
| | Dimethicone, 50 cst | 0.40% |
| Part D | Benzyl alcohol | 1.00% |

TABLE 7

| | Antioxidant Lotion | |
|---|---|---|
| Part A | Usp purified water | 58.54% |
| | Acrylates/c10-30 alkyl acrylate crosspolymer | 0.30% |
| Part B | Propylene glycol | 5.00% |
| | Disodium EDTA | 0.01% |
| | Triethanolamine, 99% | 0.35% |
| Part C | Octyl palmitate | 29.00% |
| | Pvp/eicosene copolymer | 2.00% |
| | Stearic acid | 0.50% |
| | Polyglyceryl-3 distearate | 0.29% |
| | Methylparaben | 0.30% |
| | Sorbitan isostearate | 0.71% |
| | Vitamin E, dl alpha tocopherol | 0.50% |
| | Diethylhexyl syringylidene malonate | 0.90% |
| | Propylparaben | 0.10% |
| | Dimethicone, 50 cst | 0.40% |
| Part D | Benzyl alcohol | 1.00% |

A water phase was created by adding Acrylates/C10-30 Alkyl Acrylate Crosspolymer to water of Part A while stirring and mixed until clear and lump-free. While mixing, the propylene glycol and disodium EDTA were added to the water phase mixture of Part A and mixed well for 10 minutes. Triethanolamine of Part B was then added to the water phase mixture and continued mixing well. Separately an oil phase was created by mixing the ingredients of Part C together and heat to 140-145° F. while mixing well. The oil phase was then added to the water phase and continued mixing to form an emulsion. The emulsion was cooled to room temperature and then benzyl alcohol of part D was added to the cool emulsion and mixed thoroughly. Additional water was added QS to weight. The difference between the placebo and experimental formulation was the addition of antioxidants into the oil phase.

Figure 6B:
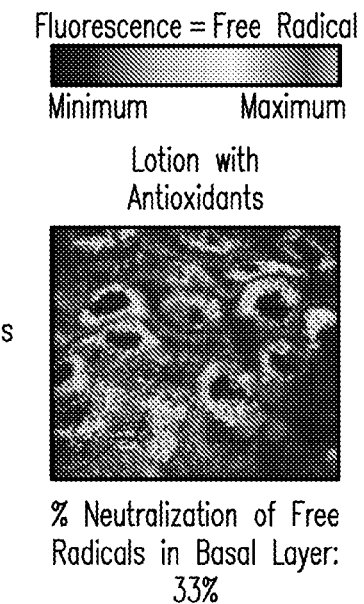
Figure 6C:
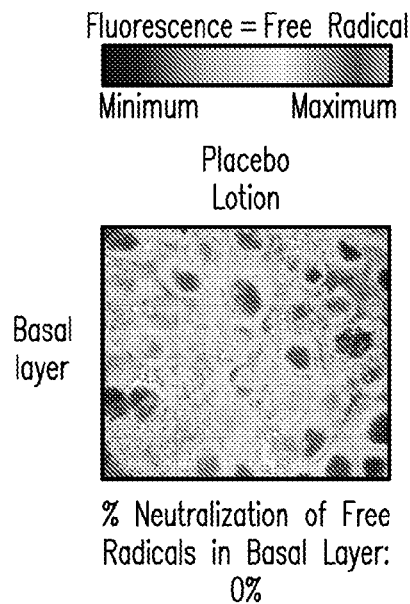
Figure 6D:
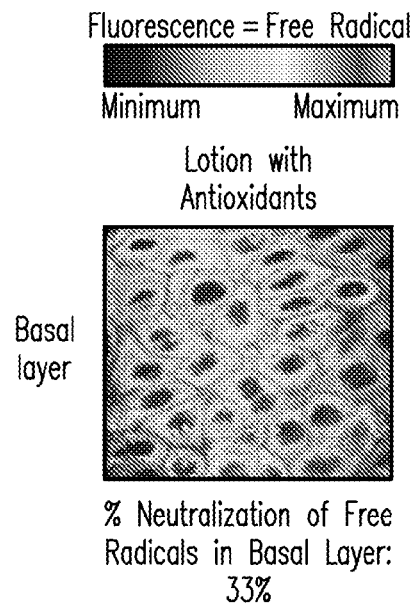

As shown in the Table 8 and FIGS. 5 and 6, in vitro ROS results demonstrate that a lotion containing both Vitamin E and Oxynex® ST together provided substantially higher protection from UV-induced ROS formation than can be achieved by Vitamin E and Emblica.

TABLE 8

| Antioxidant | % ROS Neutralized in the Basal Layer |
|---|---|
| After 1 MED Exposure | |
| 0.5% vitamin E + 0.1% Emblica | ND |
| 0.5% vitamin E + 0.9% Oxynex ST | 47 |
| After 4 MED Exposure | |
| 0.5% vitamin E + 0.1% Emblica | 5 |
| 0.5% vitamin E + 0.9% Oxynex ST | 33 |

ND = not determined.

The addition of Oxynex® ST to a lotion containing Vitamin E neutralized 33% ROS after exposure to 4 MED of UVR and neutralized 47% ROS after 1 MED UVR within the basal layer. These results are significantly better than 5% ROS neutralization for a lotion containing only Vitamin E and Emblica.

The compositions containing the combination of 0.5% Vitamin E and 0.9% Oxynex® ST were also tested in the lipid peroxidation tests described above and shown to prevented UV-induced lipid peroxidation by 75%. This is comparable to results obtained for 0.5% Vitamin E plus 0.1% Emblica. However, although the compositions were similar in ability to inhibit lipid peroxidation, by combining Vitamin E with Oxynex® ST we have observed an unexpected increase in protection from ROS formation across the full thickness of epidermis.

These results also confirm that Oxynex® ST maintains its antioxidant capability within skin when exposed to UVR as opposed to becoming a pro-oxidant. Taken together, these results demonstrate the unexpected benefits of combining Vitamin E with Oxynex® ST for protection against UV-induced ROS formation within the full thickness of epidermis.

Cosmetic Clinical Efficacy Evaluation of High SPF Antioxidant Formulation

Two topical antioxidant sunscreen formulation were generated according to the methods of the invention containing the sunscreen and antioxidant loads:

| Ingredient | SPF 70 | SPF 30 |
|---|---|---|
| Sunscreen | | |
| Homosalate | 15% | 15% |
| Octocrylene | 10% | 2% |
| Avobenzone | 3% | 2% |
| Oxybenzone | 6% | 5% |
| Octisalate | 5% | 5% |
| Antioxidant | | |
| Diethylhexyl sringylidene malonate | 0.9% | — |
| Vitamin E | 0.5% | 0.5% |
| Emblica | — | 0.01% |

All percentages are w/w.

In vivo SPF testing conducted according to the U.S. F.D.A. approved testing protocols determined that the first formulation rated as at least SPF 70 and the second was at least SPF 30. For convenience they will be referred to herein as SPF 70 and SPF 30. Methods of in vitro and in vivo measurement of SPF are describe, e.g., in U.S. Patent Application Publication Nos. 20070160549 and 20080081024.

A clinical efficacy evaluation was conducted to determine the effect of the high SPF antioxidant formulations produced as described above on various indications of skin health including, skin dryness (moisture), skin texture (roughness, smoothness), elasticity (i.e., firmness or resiliency), skin tone and clarity, uniformity of pigmentation, fine lines and wrinkles, erythema, photodamage, and hidden damage (subclinical pigmentation). The study is a single-blind, parallel, randomized, controlled, twelve (12) week use test with an additional baseline equilibration period of seven (7) days. One-hundred-nine (109) subjects were enrolled and one-hundred-five (105) continued on the study. Four (4) subjects were discontinued due to inability to make all regularly scheduled visits. No adverse experiences have been reported. The results below demonstrate significant improvement over baseline condition of the skin as a result of 12 weeks of use of the tested products.

Qualified subjects were divided into two (2) product groups and an untreated control group. An expert clinical evaluator graded the face of each subject at each visit to assess individual parameters that contribute to the visual and tactile properties of premature aging, as well as to provide an overall global assessment of degree of visible photodamage. The clinical grading scores at baseline were used to confirm that the subject presents with mild to moderate photo-damage and therefore were qualified for participation.

Specific attributes were quantified using bioinstrumentation; silastic resin replicas with image analysis to also measure fine lines and wrinkles, a Nova Meter for determining moisture content, and a Dermalab suction device to measure skin elasticity. A trained photographer photographed each subject at baseline, 2, 4, 8 and 12 weeks using a fixed angle standard and cross-polarized light Canfield clinical camera apparatus to document appearance of a specific site on the side of the face (including crow's feet area). The photographer took full facial UV reflected photographs, at baseline and at the 12-week visit or until the product had washed out and no longer fluoresces (whichever was later). The expert clinical evaluator graded the UV photographs taken at baseline and 12-weeks (±days to washout) to assess degree of subclinical "hidden" damage present and then globally assessed the amount of change compared to baseline.

Test compositions were overwrapped to hide the identity of the manufacturer and labeled with the appropriate test article codes and use directions. Approximately one-half the study product was delivered prior to the start of the study and the second half of the product was delivered prior to the midpoint of the study.

Seven to ten days prior to initiation of the treatment period, subjects underwent a baseline equilibration period, during which they discontinued the use of all facial sunscreens, skin treatment products, their current facial cleansing bar or cream, and any moisturizing facial cosmetic products; use Camay soap daily, each morning for any facial cleansing and as needed throughout the day; and refrain from use of tanning beds for the duration of the study.

Following the equilibration period, subjects were qualified by presenting with sufficient signs of dryness and extrinsic skin aging. Following qualification, subjects were randomly assigned to one of two test groups or to the untreated control group. For the duration of the study subjects assigned to both the treatment and non-treatment groups wash their faces only with the Camay soap provided. Subjects in both of the treatment groups applied the assigned test article to their face (and neck if desired) once daily (each morning), then reapply as needed.

Subjects recorded application times each day on a diary provided by the study site at each visit. Subjects in the non-treatment group recorded the number of times that they cleanse and apply their usual moisturizer, sunscreen and color cosmetic products during the study. Diaries were collected and redistributed in the same manner as outlined for the treatment groups.

All subjects had clinical skin evaluations, Nova Meter, Dermalab, Silastic resin replicas, and standard light photography after 2, 4, 8 and 12 weeks. Subjects have UV photos taken only at baseline and 12 weeks (±days for washout) by an expert clinical evaluator who was not aware of product assignment, nor which subjects were in the treatment groups and which subjects were in the non-treated control group.

Evaluations were made at each visit for several indicators of photodamage listed below. Grading scales are outlined in each of the categories A. Overall Assessment of Degree of Photodamage.

Subjects were graded on a scale of 0-10 with 0 representing no photodamage and 10 representing severe photodamage. The results were as follows:

TABLE 9

| | MEAN OVERALL PHOTODAMAGE SCORE ± S.D. (% IMPROVEMENT) | | |
|---|---|---|---|
| | SPF 30 | SPF 70 | CONTROL |
| BASELINE | 4.80 ± 0.97 (n = 39) | 4.72 ± 0.84 (n = 39) | 4.71 ± 0.79 (n = 27) |
| WEEK 2 | 4.41 ± 0.73* (8) (n = 39) | 4.45 ± 0.51* (5) (n = 39) | 4.44 ± 0.60* (6) (n = 27) |
| WEEK 4 | 4.04 ± 0.62* (16) (n = 39) | 4.15 ± 0.68* (12) (n = 39) | 4.14 ± 0.60* (12) (n = 27) |
| WEEK 8 | 4.40 ± 0.70* (8) (n = 39) | 4.42 ± 0.51* (6) (n = 37) | 4.48 ± 0.64$^T$ (5) (n = 26) |
| WEEK 12 | 3.97 ± 0.49* (17) (n = 39) | 3.86 ± 0.38* (18) (n = 39) | 3.95 ± 0.38* (16) (n = 27) |

*Significantly different than baseline value, $p \leq 0.050$.
$^T$Trendwise significantly different than baseline value, p-0.150-0.051.

B. Facial Dryness.

Subjects were given grades of 0-4 as follows:
  0 normal skin; no signs of dryness
  1 mild dryness; slight but definite dryness, fine scaling present may have a powdery or ashy appearance
  2 moderate dryness; somewhat coarser scaling, some cracking evident as uplifted scales.
  3 marked dryness; marked coarse scaling, cracking evident as uplifted scales.
  4 severe dryness; very marked; very coarse scaling; cracking progressing to fissuring; erythema may be present.

The results were as follows:

TABLE 10

| | MEAN DRYNESS SCORE ± S.D. (% IMPROVEMENT) | | |
|---|---|---|---|
| | SPF 30 | SPF 70 | CONTROL |
| BASELINE | 0.97 ± 0.16 (n = 39) | 1.05 ± 0.22 (n = 39) | 1.07 ± 0.26 (n = 27) |
| WEEK 2 | 0.20 ± 0.52* (79) (n = 39) | 0.23 ± 0.48* (78) (n = 39) | 0.11 ± 0.32* (90) (n = 27) |
| WEEK 4 | 0.12 ± 0.40* (88) (n = 39) | 0.15 ± 0.36* (86) (n = 39) | 0.18 ± 0.48* (83) (n = 27) |

TABLE 10-continued

| | MEAN DRYNESS SCORE ± S.D. (% IMPROVEMENT) | | |
|---|---|---|---|
| | SPF 30 | SPF 70 | CONTROL |
| WEEK 8 | 0.33 ± 0.57* (66) (n = 39) | 0.10 ± 0.31* (91) (n = 37) | 0.26 ± 0.53* (76) (n = 26) |
| WEEK 12 | 0.00 ± 0.00* (100) (n = 39) | 0.00 ± 0.00* (100) (n = 39) | 0.11 ± 0.32* (90) (n = 27) |

C. Texture (Roughness/Smoothness)

Subjects were graded from a score of 0, indicating smooth, even surface, to 10 indicating a rough, coarse, uneven surface. The results were as follows:

TABLE 11

| | MEAN TEXTURE SCORE ± S.D. (% IMPROVEMENT) | | |
|---|---|---|---|
| | SPF 30 | SPF 70 | CONTROL |
| BASELINE | 3.68 ± 0.69 (n = 39) | 3.86 ± 0.61 (n = 39) | 3.64 ± 0.63 (n = 27) |
| WEEK 2 | 2.24 ± 1.00* (39) (n = 39) | 2.56 ± 0.94* (34) (n = 39) | 2.35 ± 1.02* (35) (n = 27) |
| WEEK 4 | 2.58 ± 0.97* (30) (n = 39) | 2.25 ± 1.17* (42) (n = 39) | 2.30 ± 1.02* (37) (n = 27) |
| WEEK 8 | 2.62 ± 0.87* (29) (n = 39) | 2.88 ± 0.95* (25) (n = 37) | 2.70 ± 0.87* (26) (n = 26) |
| WEEK 12 | 2.52 ± 0.74* (32) (n = 39) | 2.35 ± 0.73* (39) (n = 39) | 2.64 ± 0.64* (28) (n = 27) |

*Significantly different than baseline value, $p \leq 0.050$.

D. Elasticity/Firmness/Resiliency

Subjects were graded from a score of 0, indicating firm, resilient, taut skin, to 10 indicating skin that was loose, flaccid, no turgor. The results were as follows:

TABLE 12

| | MEAN ELASTICITY/FIRMNESS/RESILIENCY SCORE ± S.D. (% IMPROVEMENT) | | |
|---|---|---|---|
| | SPF 30 | SPF 70 | CONTROL |
| BASELINE | 5.16 ± 1.13 (n = 39) | 5.18 ± 0.94 (n = 39) | 5.21 ± 1.03 (n = 27) |
| WEEK 2 | 4.24 ± 1.13* (18) (n = 39) | 4.19 ± 1.06* (19) (n = 39) | 4.21 ± 1.20* (19) (n = 27) |
| WEEK 4 | 4.15 ± 0.97* (20) (n = 39) | 4.00 ± 0.80* (23) (n = 39) | 4.30 ± 1.08* (18) (n = 27) |
| WEEK 8 | 3.77 ± 0.94* (27) (n = 39) | 3.81 ± 0.92* (26) (n = 37) | 4.05 ± 1.00* (22) (n = 26) |
| WEEK 12 | 3.33 ± 0.92* (36) (n = 39) | 3.29 ± 1.03* (37) (n = 39) | 3.67 ± 0.87* (30) (n = 27) |

*Significantly different than baseline value, $p \leq 0.050$.

E. Lines and Wrinkles

Subjects were graded from a score of 0, indicating no lines or wrinkles, to 10 indicating coarse skin containing numerous wrinkles. The results were as follows:

TABLE 13

| | MEAN FINE LINES/WRINKLES SCORE ± S.D. (% IMPROVEMENT) | | |
|---|---|---|---|
| | SPF 30 | SPF 70 | CONTROL |
| BASELINE | 4.12 ± 1.42 (n = 39) | 4.78 ± 1.32 (n = 39) | 4.44 ± 1.58 (n = 27) |
| WEEK 2 | 3.92 ± 1.18 (5) | 4.28 ± 0.72* (11) | 4.37 ± 1.21 (2) |

TABLE 13-continued

MEAN FINE LINES/WRINKLES SCORE ± S.D.
(% IMPROVEMENT)

|  | SPF 30 | SPF 70 | CONTROL |
|---|---|---|---|
|  | (n = 39) | (n = 39) | (n = 27) |
| WEEK 4 | 4.12 ± 0.95 (0) | 4.15 ± 0.80* (13) | 4.07 ± 1.29$^T$ (8) |
|  | (n = 39) | (n = 39) | (n = 27) |
| WEEK 8 | 3.55 ± 0.90* (14) | 3.75 ± 0.74* (22) | 3.81 ± 0.97* (14) |
|  | (n = 39) | (n = 37) | (n = 26) |
| WEEK 12 | 3.28 ± 0.89* (20) | 3.58 ± 0.69* (25) | 3.49 ± 1.06* (21) |
|  | (n = 39) | (n = 39) | (n = 27) |

*Significantly different than baseline value, p ≤ 0.050.
$^T$Trendwise significantly different than baseline value, p-0.150-0.051.

F. Skin Tone/Clarity

Subjects were graded from a score of 0, indicating clear, radiant, translucent skin, to 10 indicating skin that was sallow, dull and/or had uneven skin tone. The results were as follows:

TABLE 14

MEAN SKIN TONE SCORE ± S.D.
(% IMPROVEMENT)

|  | SPF 30 | SPF 70 | CONTROL |
|---|---|---|---|
| BASELINE | 5.57 ± 0.81 | 5.40 ± 0.65 | 5.44 ± 0.85 |
|  | (n = 39) | (n = 39) | (n = 27) |
| WEEK 2 | 5.07 ± 0.69* (9) | 5.11 ± 0.60* (5) | 5.33 ± 0.56 (2) |
|  | (n = 39) | (n = 39) | (n = 27) |
| WEEK 4 | 4.90 ± 0.70* (12) | 4.78 ± 0.77* (12) | 4.84 ± 0.76* (11) |
|  | (n = 39) | (n = 39) | (n = 27) |
| WEEK 8 | 4.62 ± 0.68* (17) | 4.50 ± 0.69* (17) | 4.53 ± 0.79* (17) |
|  | (n = 39) | (n = 37) | (n = 26) |
| WEEK 12 | 4.14 ± 0.75* (26) | 3.92 ± 0.80* (27) | 3.98 ± 0.62* (27) |
|  | (n = 39) | (n = 39) | (n = 26) |

*Significantly different than baseline value, p ≤ 0.050.

G. Uniformity of Pigmentation

Subjects were graded from a score of 0, indicating uniform, even pigmentation, to 10 indicating skin that was uneven, blotchy or mottled. The results were as follows:

TABLE 15

MEAN UNIFORMITY OF PIGMENTATION
SCORE ± S.D. (% IMPROVEMENT)

|  | SPF 30 | SPF 70 | CONTROL |
|---|---|---|---|
| BASELINE | 5.07 ± 0.94 | 4.90 ± 0.99 | 4.95 ± 1.09 |
|  | (n = 39) | (n = 39) | (n = 27) |
| WEEK 2 | 4.80 ± 0.74$^T$ (5) | 4.67 ± 0.77$^T$ (5) | 4.76 ± 0.73 (4) |
|  | (n = 39) | (n = 39) | (n = 27) |
| WEEK 4 | 4.99 ± 0.89 (2) | 4.81 ± 0.90 (2) | 4.84 ± 0.84 (2) |
|  | (n = 39) | (n = 39) | (n = 27) |
| WEEK 8 | 4.42 ± 0.66* (13) | 4.38 ± 0.59* (11) | 4.37 ± 0.78* (12) |
|  | (n = 39) | (n = 37) | (n = 26) |
| WEEK 12 | 4.14 ± 0.73* (18) | 4.04 ± 0.78* (18) | 3.97 ± 0.69* (20) |
|  | (n = 39) | (n = 39) | (n = 27) |

*Significantly different than baseline value, p ≤ 0.050.
$^T$Trendwise significantly different than baseline value, p-0.150-0.051.

H. Erythema

Subjects were graded from a score of 0, indicating no erythema or normal tone, to 10 indicating skin that was marked, very red. The results were as follows:

TABLE 16

MEAN NOVA METER VALUE ± S.D.
(% IMPROVEMENT)

|  | SPF 30 | SPF 70 | CONTROL |
|---|---|---|---|
| BASELINE | 202.55 ± 87.93 | 203.12 ± 88.65 | 218.92 ± 114.92 |
|  | (n = 39) | (n = 39) | (n = 27) |
| WEEK 2 | 179.17 ± 64.82$^T$ (−12) | 180.15 ± 74.05$^T$ (−11) | 196.22 ± 86.17 (−10) |
|  | (n = 39) | (n = 39) | (n = 27) |
| WEEK 4 | 160.17 ± 42.24* (−21) | 177.0 ± 72.68* (−13) | 191.74 ± 77.53 (−12) |
|  | (n = 39) | (n = 39) | (n = 27) |
| WEEK 8 | 158.97 ± 39.01* (−22) | 150.10 ± 38.63* (−26) | 166.73 ± 57.76* (−24) |
|  | (n = 39) | (n = 37) | (n = 26) |
| WEEK 12 | 169.89 ± 45.02* (−16) | 182.35 ± 60.00$^T$ (−10) | 179.59 ± 62.21* (−18) |
|  | (n = 39) | (n = 39) | (n = 27) |

*Significantly different than baseline value, p ≤ 0.050.
$^T$Trendwise significantly different than baseline value, p = 0.150-0.051.

Facial skin condition was measured on all subjects using Dermalab, Novameter and replica image analysis at baseline and weeks 2, 4, 8 and 12 as follows.

Elasticity was measured on one side of the face (same location at each visit) on all subjects using the Dermalab (Cortex Technology, Denmark), which applies a negative pressure to the skin surface and calculates the height to which the skin can be drawn up and the rate at which it returns to equilibrium thus providing a measurement of elasticity. Dermalab measurements took place on the opposite side of the face as image analysis replicas.

Moisturization was measured on one side of the face (same location at each visit) to document hydration levels of the skin surface. The relative degree of skin hydration is assessed using the Dermal Phase Meter 9003 (NOVA meter). Measurements are made by applying an alternating voltage to the skin with a closely spaced pair of electrodes and measuring the impedance. Changes in water content change the impedance of the capacitive circuit. The first two consecutive readings within 10% were recorded. The same side of the face is measured at each visit. The test room temperature and humidity will be recorded during each set of readings.

Contour (surface textural) analysis provides a method for quantifying skin augmentation, the cosmetic action of reducing lines and wrinkles. For this procedure, skin replicas made of the crow's feet area were analyzed for contour and surface texture using image analysis. Skin replicas of the crow's feet area were prepared using silastic resin impression materials (Cuderm). Silastic resin is a rapidly curing liquid applied using 1 cm diameter replica rings which stay intact after application and removal.

Facial skin condition was documented for all subjects using standard and cross polarized light photography at baseline and weeks 2, 4, 8 and 12. Hidden damage accumulated below the skin surface was evaluated by expert graders, based on UV photos taken at baseline and 12-weeks.

Digital photographs using both visible and cross-polarized light are taken of all subjects at all visits. Subjects' faces are positioned in the Canfield stereotactic repositioning apparatus and photographs are taken using the Canfield Clinical Systems camera and flash system. The camera used was a Nikon D80 SLR 35 mm model with a 60 mm macro Nikkor lens and a modified SB-23 flash head. The camera is set in Aperture priority automatic at f 16. For each subject at each time interval, a slate was photographed at 1:6 magnification identifying the subject and time interval. A frontal photo was taken at 1:6 magnification and two lateral 45° angle photos of each side of the face is taken at 1:4 and 1:3 magnification using standard lighting and repeated using cross-polarized light.

Subjects placed their heads in the Canfield stereotactic repositioning device and have photographs taken using the Canfield Clinical Systems camera system. The camera used was a Nikon 6006 SLR 35 mm model. For each subject at each time interval, a slate was photographed at 1:6 magnification identifying the subject and time interval. A frontal photo was taken at 1:6 magnification and one lateral 45° angle photo of each side of the face was taken at 1:6 magnification. Subsequently, two frontal UV-light (UV reflected) photographs were taken at 1:6 magnification employing a Kodak 18A filter over the lens, a Sunpak MS 4000 Monolight and T-Max 400 black and white print film. Exposures were taken at f8 and 1/250 sec. shutter speed.

An expert evaluator graded full facial photos individually for uniformity of pigmentation at each time-point (baseline and 12-week) grading on a scale of 0 (uniform/even) to 10 (uneven, blotchy mottled). The expert evaluator also conducted a comparative assessment of 12-week photos vs. baseline for each individual subject. Grading scales are from −4 to +4 as follows:
 −4 extreme increase in hyper pigmentation
 −3 moderate increase in hyper pigmentation
 −2 mild increase in hyper pigmentation
 −1 barely perceptible increase (worsening) in hyper pigmentation
 0 no difference between baseline and 12-week
 1 barely perceptible decrease (improvement) in hyper pigmentation
 2 mild in hyper pigmentation
 3 moderate decrease in hyper pigmentation
 4 extreme decrease in hyper pigmentation Example Formulations Example sunscreen formulations are prepared according to the methods described herein with the following ingredients:

TABLE 17

| Ingredient | Amount, % w/w |
| --- | --- |
| Purified Water | 45.0-90.0 |
| Homosalate | 5.0-15.0 |
| Octocrylene | 2.0-10 |
| Oxybenzone | 0.5-6.0 |
| Octisalate | 5.0 |
| Avobenzone | 1.0-3.0 |
| Prolipid 141 | 2.0-7.0 |
| Butylene Glycol | 2.0-7.0 |
| Microcrystalline Cellulose/ Carboxymethylcellulose | 0.2-5.0 |
| Benzyl Alcohol | 0.5-2.0 |
| Vitamin E | 0.01-3.0 |
| Diethylhexyl syrigylidene malonte | 0.01-6.0 |
| *Phylanthus Emblica* fruit extract | 0.01-1.0 |
| Green Tea Extract | 0.01-1.0 |
| Disodium Lauriminodiproprionate Tocopheryl Phosphates | 0.3-3.0 |
| Chlorphenesin | .10-0.20 |
| Butylated PVP | .05-.50 |
| Disodium EDTA | 0.01-.20 |
| Sodium Ascorbyl Phosphate | .01-1.0 |
| Vitamin A Palmitate | .01-1.0 |

What is claimed is:

1. A topical antioxidant sunscreen formulation comprising about 15% (w/w) homosalate, about 10% (w/w) octocrylene, about 3% avobenzone, about 6% (w/w) oxybenzone, and about 5% (w/w) octisalate, and an antioxidant mixture comprising about 0.9% (w/w) diethylhexyl syringylidene malonate and about 0.5% (w/w) Vitamin E.

2. A method for treating or preventing photodamage of skin of a subject in need thereof, which comprises applying the composition of claim 1 to the subject's skin that will be or has been exposed to UVR.

* * * * *